(12) United States Patent
Suzuki et al.

(10) Patent No.: US 11,275,053 B2
(45) Date of Patent: Mar. 15, 2022

(54) METHOD AND PROGRAM FOR APPROXIMATELY IDENTIFYING MOLECULAR STRUCTURE OF MULTICOMPONENT MIXTURE

(71) Applicants: JAPAN PETROLEUM ENERGY CENTER, Minato-ku (JP); JXTG NIPPON OIL & ENERGY CORPORATION, Chiyoda-ku (JP); IDEMITSU KOSAN CO., LTD., Chiyoda-ku (JP); COSMO OIL CO., LTD., Minato-ku (JP)

(72) Inventors: Teruo Suzuki, Chiba (JP); Keita Katano, Chiba (JP); Ryuzo Tanaka, Chiba (JP); Shogo Teratani, Chiba (JP)

(73) Assignees: JAPAN PETROLEUM ENERGY CENTER, Minato-ku (JP); ENEOS Corporation, Chiyoda-ku (JP); IDEMITSU KOSAN CO., LTD., Chiyoda-ku (JP); COSMO OIL CO., LTD., Minato-ku (JP)

( * ) Notice: Subject to any disclaimer, the term of this patent is extended or adjusted under 35 U.S.C. 154(b) by 0 days.

(21) Appl. No.: 16/340,883

(22) PCT Filed: Mar. 27, 2018

(86) PCT No.: PCT/JP2018/012447
§ 371 (c)(1),
(2) Date: Apr. 10, 2019

(87) PCT Pub. No.: WO2018/181320
PCT Pub. Date: Oct. 4, 2018

(65) Prior Publication Data
US 2019/0353616 A1 Nov. 21, 2019

(30) Foreign Application Priority Data
Mar. 29, 2017 (JP) .............................. JP2017-066425

(51) Int. Cl.
*G01N 27/622* (2021.01)
*G16C 20/40* (2019.01)
(Continued)

(52) U.S. Cl.
CPC ....... *G01N 27/622* (2013.01); *G01N 33/2835* (2013.01); *G16C 20/40* (2019.02); *H01J 49/0095* (2013.01)

(58) Field of Classification Search
None
See application file for complete search history.

(56) References Cited

U.S. PATENT DOCUMENTS 8,975,084 B2 * 3/2015 Qian .................. H01J 49/0045
                                              436/173
2005/0103991 A1  5/2005 Walk et al.
(Continued)

FOREIGN PATENT DOCUMENTS

JP  2006-23184 A   1/2006
JP  2006-527371 A  11/2006
(Continued)

OTHER PUBLICATIONS

International Search Report dated Jun. 26, 2018 in PCT/JP2018/012447 filed Mar. 27, 2018.
(Continued)

*Primary Examiner* — Xiaoyun R Xu
(74) *Attorney, Agent, or Firm* — Oblon, McClelland, Maier & Neustadt, L.L.P.

(57) ABSTRACT

A method identifies the molecular structure of each component in a multicomponent mixture. The method includes (1) subjecting the multicomponent mixture to mass spectrometry to identify the formula of a molecule attributed to each obtained peak, and to identify abundance of the molecule; (2) subjecting the multicomponent mixture to collision
(Continued)

induced dissociation; (3) performing mass spectrometry on each fragment ion generated via the collision induced dissociation in (2) to identify the core structure forming each fragment ion and abundance thereof; (4) dividing the molecules attributed to each peak in (1) into "classes" based on "a type and number of heteroatoms, and a DBE value", and on all the molecules belonging to each "class", estimating the existence state and abundance thereof; and (5) determining the core structure forming each molecule, for which the existence state is estimated in (4), and determining and assigning a side chain and a cross-link thereto.

19 Claims, 8 Drawing Sheets

(51) Int. Cl.
  *G01N 33/28* (2006.01)
  *H01J 49/00* (2006.01)

(56) References Cited

U.S. PATENT DOCUMENTS

| 2008/0142695 | A1 | 6/2008 | Joshi et al. |
| 2012/0153139 | A1 | 6/2012 | Qian et al. |
| 2013/0187036 | A1 | 7/2013 | Mennito et al. |
| 2013/0206980 | A1 | 8/2013 | Mennito et al. |
| 2014/0231641 | A1 | 8/2014 | Qian et al. |

FOREIGN PATENT DOCUMENTS

| JP | 2013-190422 A | 9/2013 |
| JP | 2014-500506 A | 1/2014 |
| JP | 2014-503816 A | 2/2014 |
| JP | 2014-41142 A | 3/2014 |
| WO | WO 2004/108742 A1 | 12/2004 |
| WO | WO 2012/082504 A2 | 6/2012 |
| WO | WO 2012/083095 A2 | 6/2012 |
| WO | WO 2014/099312 A1 | 6/2014 |

OTHER PUBLICATIONS

"Toward high value added-petroleum refining," HP, May 7, 2016, http://www.pecj.or.jp/japanese/report/2016report/h28data/1.1(1)-1.pdf ( 8 total pages).

Tanaka, R. et al., "Outline of Petroleomics," The 53rd Proceedings of Conference on Coal Science, No. 2-29, 2016, pp. 116-117.

* cited by examiner

METHOD AND PROGRAM FOR APPROXIMATELY IDENTIFYING MOLECULAR STRUCTURE OF MULTICOMPONENT MIXTURE

TECHNICAL FIELD

The invention relates to a method for identifying a molecular structure of each component forming a multicomponent mixture by using a computer. Furthermore, the invention relates to a method for determining a composition model of the multicomponent mixture. Moreover, the invention relates to a program for allowing the computer to execute the methods.

BACKGROUND ART

In operation of various equipment relating to petroleum refinery, such a technique is ordinarily adopted as analyzing stock oil on the basis of holistic physical properties such as specific gravity, viscosity and distillation properties (a boiling point) to determine operating conditions with reference to operational performance in an oil type having similar data in the past.

However, according to this technique, it is not easy to search the similar data in the past in times in which imported crude oil types are diversified as in the present time, and further in view of improvement in operational efficiency, it only needs no longer to simply follow the operational performance in the past.

Accordingly, it has been considered that, if a chemical structure of the petroleum and abundance thereof are understood at a level of hydrocarbon molecules forming the petroleum, and not from a viewpoint grouped into a section such as the specific gravity, the viscosity and the distillation properties, and the operating conditions can be set on the basis of findings such as estimated values of physical properties obtained therefrom, further efficient operation based on objectivity can be performed. Therefore, in a petroleum industry, an advent of a technology for understanding the petroleum at a molecular level has been long awaited.

However, the petroleum is a mixture consisting of a vast number of hydrocarbon molecules, and therefore particularly in heavy oil, it has been significantly difficult to identify a chemical structure on each such molecule and to identify also the abundance.

So far, in analyzing the petroleum at the molecular level to conduct analysis on the chemical structure, a technology of measuring molecular weight with high accuracy by using a mass spectrometer according to a Fourier transform ion cyclotron resonance system as a high resolution mass spectrometer has been used. For example, such a method includes the method described in Patent Document 1 or Patent Document 2.

In particular, Patent Document 2 describes a method of estimating a molecular structure, in which molecules forming petroleum are allowed to collide with argon or the like to cut cross-linked parts in the molecule to be decomposed into core parts forming the molecule, thereby determining the chemical structure, and then combining the core parts to reconstruct an original molecule.

RELATED ART DOCUMENT

Patent Documents

Patent Document 1: JP-T-2014-500506
Patent Document 2: JP-T-2014-503816

SUMMARY OF THE INVENTION

Problems to be Solved by the Invention

However, according to the method described in Patent Document 2, on parts forming a molecule, such as a core, a cross-link and a side chain, how to construct the molecule by selecting which parts and which parts and combining which parts is determined on the basis of probability. Therefore, even if construction work of a molecular structure of components is performed in the same step on the basis of certain mass spectrometry data, the obtained results have been different each time of the construction work. Such inconvenience has been unavoidable, as long as a concept of "probability" is used in construction of the molecular structure. More specifically, according to the method described in Patent Document 2, constancy or reproducibility of the obtained results is not secured, and a critical defect "operation stability of the equipment is unable to be ensured" has remained.

In the conventional technology, a systematic theory and device for constructing the molecular structure have been unable to be devised, and therefore a so-called substantially uncertainty lingering approach called a probability theory has been inevitably accepted and used. More specifically, in a special object of the petroleum being a mixture of a vast number of types of hydrocarbon molecules of hundreds of thousands of types or more, an effective theory according to which a purpose of identifying a structure of individual molecules and abundance thereof can be attained has been unable to be constructed, and a possible method other than introducing the "probability theory" has been unable to be found under actual circumstances.

The invention has been made under such a situation, and an objective of the invention is to provide a method for identifying a molecular structure of each component forming a multicomponent mixture with predetermined accuracy by using a computer. Moreover, another objective thereof is to provide a method for determining a composition model of the multicomponent mixture. Moreover, another objective thereof is to provide a program for allowing the computer to execute the methods.

Furthermore, another objective of the invention is to provide a method for estimating values of physical properties of the multicomponent mixture on the basis of the molecular structure of each component forming the multicomponent mixture and abundance thereof, which are identified according to the method. Moreover, another objective thereof is to provide a method of operating equipment relating to the multicomponent mixture, particularly to the petroleum, in which operating conditions are set on the basis of the values of physical properties of the multicomponent mixture estimated according to such a method.

Solution to Problem

In order to achieve the objectives described above, the present inventors have created the invention described below.

One aspect of the invention is a method for identifying a molecular structure of each component forming a multicomponent mixture and abundance thereof by using a computer, comprising:

a step 1 of subjecting the multicomponent mixture to mass spectrometry to identify a molecular formula of a molecule attributed to each obtained peak, and to further identify the abundance of the molecule;

a step 2 of subjecting the multicomponent mixture to collision induced dissociation;

a step 3 of performing mass spectrometry on each fragment ion generated by means of the collision induced dissociation in the step 2 to identify a structure of a core forming each fragment ion and abundance thereof;

a step 4 of dividing the molecules attributed to each peak in the step 1 into "classes" on the basis of "a type and the number (including zero) of hetero atoms and a DBE value" and on all the molecules belonging to each "class", estimating a state of existence and the abundance, and a step 5 of determining a structure of a core forming each molecule on each molecule in which the state of existence is estimated in the step 4, and further determining and assigning a side chain and a cross-link thereto.

Moreover, another aspect of the invention is a method for determining a composition model of the multicomponent mixture, and a program for allowing the computer to execute the methods.

Further, another aspect of the invention is a method for estimating values of physical properties of the multicomponent mixture on the basis of the molecular structure of each component forming the multicomponent mixture and the abundance thereof, which are identified according to the method, and a method of operating equipment relating to the multicomponent mixture, preferably to the petroleum, in which operating conditions are set on the basis of the values of physical properties of the multicomponent mixture estimated according to such a method.

In identifying the molecular structure of each component forming the multicomponent mixture, the invention has been made on the basis of construction of a new innovative theory on deep insight and various brilliant views based on wide wisdom on mass spectrometry.

In each step included in the method of the invention, various original rules and assumptions are ingeniously set. However, the rules and the assumptions are invented as a result of thoroughly conducting study on "necessary and sufficient effectiveness can be realistically secured by seizing what points", and not set without a technical basis.

Furthermore, the present inventors have closely conducted study on each of a vast number of molecules forming the petroleum as to what level of details and accuracy needs to be ensured in a chemical structure, and as a result, have invented an innovative indication system called "JACD" described later. The "JACD" is a new system for indicating structural information of the molecule, and structural information on a macromolecule such as an asphaltene molecule has been able to be obtained at a necessary and sufficient level by creating this system.

Thus, the method of the invention is a so-called "deterministic" method based on ingeniously fusing theories and various creations invented by the present inventors, and not a conventional method involving uncertainty of "probability theory".

Advantageous Effects of the Invention

The invention includes a method for identifying a molecular structure by using a "deterministic" approach, and therefore identical results are reliably obtained each time. A wording "deterministic" is used on the basis of such a fact. This wording ensures that the same results are always obtained in analysis of a raw material in operating petroleum refinery equipment, and contribution to ensuring stability is immeasurable.

Moreover, in the invention, the molecular structure, namely, various atomic groups existing in a molecule are identified on each component forming a multicomponent mixture, and therefore if a publicly-known atomic group contribution method is used, various values of physical properties of the molecule can be estimated with significantly high accuracy. Further, abundance of each component is also identified, and therefore if the abundance is taken into consideration, values of physical properties of the multicomponent mixture as a whole can also be estimated from the values of physical properties of each component.

In the petroleum refinery equipment in which optimum conditions are ordinarily set for various values of physical properties of stock oil as a direct or indirect guideline, and operation is performed, various values of physical properties with high accuracy obtained according to the method of the invention can be used, which contributes to further improved efficiency.

Thus, the invention is an innovative art according to which a difficult problem essentially involved in the conventional technology can be solved, and an extraordinary effect can be produced in view of application to an actual petroleum industry.

MODE FOR CARRYING OUT THE INVENTION

Figure 1:
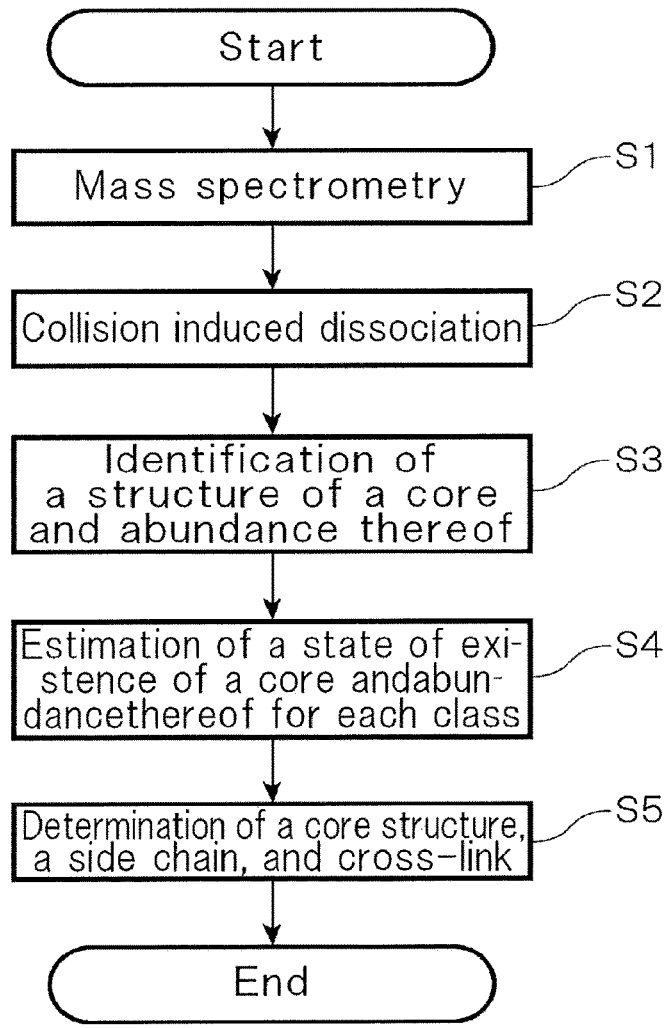
FIG. 1 shows a flowchart describing a method according to an embodiment of the invention.

Hereinafter, an embodiment of the invention will be described.

First, a term and an expression as used herein will be described.

(1) "Multicomponent Mixture"

A term "multicomponent mixture" is a concept covering all mixtures consisting of two or more components. A content ratio of the component is irrelevant. Specifically, the term preferably means "petroleum", and further preferably means "heavy oil".

In the invention, more specifically, the term means a "mixture containing a great number of aromatic compounds as a main component".

(2) "Component", "Form"

A term "component" in "each component forming the multicomponent mixture" is preferably viewed as each single constituent forming the multicomponent mixture, and an "aggregate of molecules recognized to belong to identical molecular species". Here, a term "identical" may be viewed in a meaning "a molecular structure is perfectly identified and identical on the basis", or may be viewed in a meaning "isomers (same in a molecular formula, but different in structures) with each other on the molecular structure are deemed to be identical", or may be viewed in a meaning "identical in a structure identified by a system such as JACD" described later. Furthermore, the term may be viewed widely in a meaning the "aggregate of molecules grouped on the basis of an arbitrarily specified reference".

Moreover, a term "form" need not be used in assuming whole 100% components existing in the multicomponent mixture. "Each component forming the mixture" may be appropriately determined according to necessity of identifying a molecular species as the component at what level of details depending on how to use the molecular structure of each component identified by the invention. For example, only the molecular species having a predetermined content (abundance) or more in the multicomponent mixture is targeted, and viewed as "the component forming the mixture". Necessity of identifying the molecular structures on all of vast types of molecular species as in the petroleum is not necessarily high and a molecular species existing only in a trace amount may be neglected when necessary. For example, in a place in which, as the "multicomponent mixture", polycyclic aromatic resin fraction (PA) is described as a target in the present specification, the description with neglecting existence of a paraffin-based compound and an olefin-based compound as the component forming polycyclic aromatic resin fraction (PA) is found in several places.

(3) "Identify the Molecular Structure", "Molecule"

An expression "identify the molecular structure" involves all actions, as long as any action of identifying any information on the structure of the molecule is taken on the "molecule" in the "component" described above. A degree of theoretical accuracy or a way of indication on the identified structure is irrelevant, in particular. According to the purpose and the necessity, the degree and the way of indication may be appropriately selected. The expression includes not only the action of identifying the structure of the molecule as a whole, but also the action of identifying the structure by incorporating information on the structure of part of the molecule thereinto. For example, such a way of identification also corresponds thereto as identifying only the structure of a core part and leaving a side chain part or a cross-linked part as the molecular formula without identifying the structure thereof.

The way of identifying the structure is preferably performed according to an indication system called JACD described later. In the present specification, a case where an expression "the molecular structure is identified" is described preferably means that the molecular structure is identified by JACD. The molecule identified in the structure by "JACD" has a concept including all the isomers depending on a difference in bonding positions of attributes described later.

In the present specification, a wording "molecule" may be viewed as the concept including all the isomers.

(4) "Identify Abundance of Each Component"

In an expression "identify abundance of each component", accuracy is irrelevant, as long as the action of identifying a ratio at which each component exists is taken on each component forming the mixture. Moreover, the expression does not mean that the abundance of all component species forming the mixture should be identified. More specifically, the expression does not mean that the action "identify the abundance of each component" is achieved only when the abundance of all the components is identified, including such a component as existing only in an amount to a degree at which detection is difficult by an analysis technology or a component unnecessary to be identified. Such a trace component and the like may be collectively treated as "any other components". Furthermore, the trace component and the like may be excluded from the range of "each component forming the mixture", and needs not to be included in a denominator in calculating the abundance of any other components.

(5) "All"

If a wording "all" herein is literally viewed as a meaning of "perfectly whole 100%", the invention is liable not to effectively produce an effect as an art. Moreover, accuracy of the description of the present specification is liable not to be secured.

Therefore, for example, a place referred to as "all the peaks" on a mass spectrum may be viewed not only in a meaning of literally "perfectly whole 100% peaks", but also in a meaning of referring to other peaks in appropriately excluding the peaks relating to the molecules that are not necessarily required for the purpose of study in the situation, the peaks which are difficult to discriminate, or the like, for example. Moreover, a place referred to as "all the cores" is also viewed in a similar manner, and the place means not only "perfectly whole 100% cores", but also means that the cores may be appropriately selected or excluded according to the accuracy required and the purpose.

(6) "Peak"

A horizontal axis of the peak to be obtained in mass spectrometry indicates m/z of a molecular ion or a quasi-molecular ion of each component forming the multicomponent mixture. A numerical value represented by the m/z is a numerical value corresponding to mass of the molecular ion or the quasi-molecular ion, and therefore generally represents molecular weight of the molecule attributed to the peak.

In addition, exact representation of m/z is made in italics, but m/z is represented herein using a regular font for convenience in restrictions of character types used as a document for patent application.

In the present specification, "the peak of m/z of the molecular ion or the quasi-molecular ion obtained in the mass spectrometry" is referred to as "the peak obtained in the mass spectrometry" or simply "the peak" in several cases.

A height of the peak represents relative abundance of the molecule attributed to the peak.

(7) "Molecular Formula"

A term "molecular formula" means a formula indicating only a type and the number of elements forming the molecule, in which the structure is not identified. The type and the number of elements forming the molecule are known, and therefore information on the molecular weight and a DBE value described later or the like can be obtained.

In the mass spectrometry according to a Fourier transform ion cyclotron resonance system (referred to as "FT-ICR-mass spectrometry" in several cases) mainly used in the invention, a value of m/z can be determined to a four decimal place. Therefore, the molecular formula of the molecule attributed to the peak can be determined by fixing the number of accurate mass also in consideration of existence of an isotope of an atom. The molecular formula only represents the type and the number of elements forming the molecule, and therefore a plurality of isomers may exist as the molecule corresponding to the molecular formula determined as described above. More specifically, the plurality of isomers having the identical molecular formula are attributed to one peak.

However, in characteristics of the FT-ICR-mass spectrometry, even if the molecular formula is identical, for example, the molecular ion is different in mass from an original molecular ion by addition of a hydrogen ion to the molecular ion or the like, and therefore the molecule ion appears as another peak in several cases. Thus, if the type and the number of elements constituting the molecular formula are identical, even the molecule ion which appears as another peak in measurement may be viewed as the molecular ion of "one identical molecular formula". In a wording "the molecule corresponding to the molecular formula", a term "the molecular formula" may be viewed in a meaning of such "one identical molecular formula". Moreover, a case where a term "a certain peak" is described may be considered as a concept collectively viewing all various peaks of m/z deemed as representing "one identical molecular formula" in the meaning described above.

(8) "Core", "Single Core", "Double Core"

A term "core" means a type of "attribute" described in a section of "JACD" described later, and specific examples include an aromatic ring or a naphthene ring per se, a type in which an aromatic ring and a naphthene ring are directly bonded, and not through a cross-link, and a type in which a hetero ring is directly bonded to an aromatic ring or a naphthene ring, and not through a cross-link. The cross-link or the side chain is the attribute different from the core, and therefore a wording "core" means a type having neither the cross-link nor the side chain at all.

Meanwhile, a term "single core" has a concept referring to the molecule having only one core described above. The term is the concept referring to the molecule, and therefore also involves a type in which the side chain is bonded to the core. A molecule formed by cross-linking two or more cores described above is referred to as a "multicore". The "multicore" also means the molecule, and therefore also involves the type in which the side chain is bonded to the core. Incidentally, a molecule formed by cross-linking two cores is referred to as a "double core".

For example, a naphthalene molecule shown below consists of one fused aromatic ring, and therefore is the "single core", and is not the double core consisting of two benzene rings.

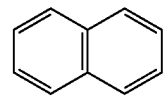

(9) "DBE Value"

A term "DBE value" means a value calculated by the following formula (I when the molecular formula is "CcHhNnOoSs".

$$DBE = c - h/2 + n/2 + 1 \qquad (1)$$

(where, c represents the number of carbon atoms, h represents the number of hydrogen atoms, n represents the number of nitrogen atoms, o represents the number of oxygen atoms, and s represents the number of sulfur atoms.)

This Value generally indicates unsaturability in the molecule, above all, a degree of existence of a double bond and a ring.

(10) "JACD" "Juxtaposed Attributes for Chemical-Structure Description"

A term "JACD" means a new indication system relating to the molecular structure, in which the structure of the molecule is indicated by the type of the attribute and the number of the attributes. JACD does not indicate any information as to in what position the attribute is bonded to other attributes.

In the above description, a term "attribute" has a concept referring to parts forming the molecule on the chemical structure. In the aromatic compound, specifically, the term refers to the "core, the "cross-link" and the "side chain" described above.

The present inventors have invented the indication system as a result of closely conducting study on each of a vast number of molecules forming the petroleum as to with what level of details the structures are necessarily and sufficiently identified.

Originally, a case where the molecule is indicated has a system including a molecular formula, a rational formula and a structural formula, and an information content on the chemical structure increases in this order. In the case of the petroleum being the mixture of a wide variety of molecules including a macromolecule, it is virtually impossible to accurately identify the structural formula on each single molecule existing therein.

Accordingly, the present inventors have invented the new indication system called "JACD". The JACD will be described by taking the molecule represented by the following chemical formula as an example.

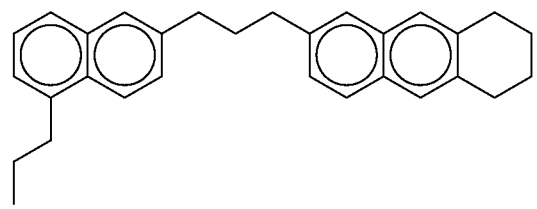

JACD represents this compound as shown in Table 1 below.

TABLE 1

| Type of attribute | Number of attributes |
|---|---|
|  (Side chain) | 1 |
|  (Cross-link) | 1 |
| 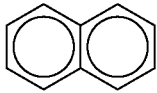 (Core) | 1 |
| 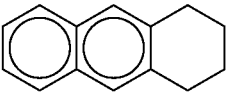 (Core) | 1 |

The molecule represented, and identified in the structure by JACD has the concept of including all the isomers depending on the difference in the bonding positions of the attributes.

(11) "Values of Physical Properties"

Specific examples of "values of physical properties" include the following values, but are not limited thereto. The values obtained on the basis of the molecular structure and the abundance identified by the method described above, and if the values express physical or chemical nature, properties or characteristics of a substance, are to be included in the values of physical properties, regardless of a name.

Specific examples include formation Gibbs free energy, ionization potential, polarizability, permittivity, vapor pressure, liquid density, API degree, gas viscosity, liquid viscosity, surface tension, boiling point, critical temperature, critical pressure, critical volume, heat of formation, heat capacity, dipole moment, enthalpy and entropy.

(12) "Petroleum", "Equipment Relating to the Petroleum"

A wording "petroleum" herein is to be used as a generic concept including crude oil, and also various fractions obtained by distilling the crude oil, fractions obtained by applying treatment such as reforming and cracking to various fractions by secondary equipment, and the like. Alternatively, the wording means a fractionated product obtained by further fractionating a certain fraction obtained by distilling the crude oil into components such as saturated hydrocarbon and aromatic hydrocarbon in several cases.

A term "equipment relating to the petroleum" includes all equipment relating to treatment of the petroleum, including distillation equipment and extracting equipment, and equipment involving a chemical reaction, such as reforming equipment, hydrogenation reaction equipment and desulfurization equipment. The "equipment relating to the petroleum" is generally referred to as "petroleum refinery equipment" in several cases.

Next, each step in the embodiment will be described with reference to a flowchart in FIG. 1.

(1) Step 1 (Mass Spectrometry) (S1 in FIG. 1)

In a step 1, the multicomponent mixture is subjected to mass spectrometry to identify a molecular formula of a molecule attributed to each obtained peak, and to further identify abundance of the molecule. In other words, the step 1 refers to a step of subjecting the multicomponent mixture to the mass spectrometry, preferably, the FT-ICR-mass spectrometry to identify the molecular formula of the molecule attributed to each peak on all the peaks obtained, and to further identify the abundance of the molecule corresponding to the molecular formula. More specifically, in the step 1, the molecular formula of each component forming the multicomponent mixture, and the abundance of the molecule corresponding to the molecular formula are identified.

In the mass spectrometry, an ultra-high resolution mass spectrometer is preferably used. Specifically, the mass spectrometer according to the Fourier transform ion cyclotron resonance system (hereinafter, referred to as an "FT-JCR-mass spectrometer" in several cases. Moreover, a mass spectrum obtained by the FT-ICR-mass spectrometry is referred to as an "FT-ICR-mass spectrum" in several cases. Moreover, a wording "FT-ICR-mass spectrometry" is generally appropriately used in several cases. Further, these wordings are used also in the description above and Brief Description of the Drawings) is used, and measurement with high accuracy is performed by using a publicly-known method, namely, by forming the molecular ion or the quasi-molecular ion by performing soft ionization to a sample.

According to the FT-ICR-mass spectrometry, the value of m/z can be determined to the four decimal place. Therefore, the molecular formula of the molecule attributed to the peak can be determined by fixing the number of accurate mass also in consideration of existence of the isotope of the atom. A plurality of molecules having an identical molecular formula are attributed to one peak.

A ratio of a height of a certain peak to a total of heights of all the peaks represents the abundance of the molecule attributed to the peak.

(2) Step 2 (Collision Induced Dissociation) (S2 in FIG. 1)

In a step 2, the multicomponent mixture is subjected to collision induced dissociation.

A term "collision induced dissociation (hereinafter, referred to as "CID" in several cases)" means operation of ionizing the molecule, and allowing the resulting ion to collide with an inert gas such as argon to cut a cross-link and a side chain. The molecule is ordinarily preferably provided with collision energy of 10 to 50 kcal/mol, for example, in such a manner that the cross-link and the side chain in each component forming the multicomponent mixture are cut. A material generated by cutting the cross-link and the side chain is a fragment ion for each core. This core has, as the side chain, an aliphatic group having about 0 to 4 carbon atoms unable to be cut in the collision induced dissociation in several cases.

When the multicomponent mixture is subjected to the FT-ICR-mass spectrometry, the molecular formula of the molecule forming the multicomponent mixture can be determined from m/z of the peak obtained, but information on the structure as to the molecule is formed of what type of "core" is unable to be obtained. Accordingly, if the multicomponent mixture is further subjected to the collision induced dissociation to cut the cross-link and the side chain in each molecule forming the multicomponent mixture, a type of the core existing in the multicomponent mixture as a whole can be known.

As conditions of subjecting the collision induced dissociation thereto, the multicomponent mixture is preferably provided with collision energy at which the cross-link and the side chain in the molecule can be effectively cut, for example, collision energy of 10 to 50 kcal/mol, and preferably collision energy of 20 to 40 kcal/mol.

(3) Step 3 (Identification of a Structure of Each Core and Abundance Thereof) (S3 in FIG. 1)

In a step 3, the mass spectrometry, preferably, the FT-ICR-mass spectrometry is performed on each fragment ion generated by the collision induced dissociation in the step 2 to identify a structure of a core forming each fragment ion and abundance thereof.

(a) First, on the core forming each fragment ion, a method for identifying the structure thereof will be described.

Specifically, information on the core obtained in the step 2 is matched with information on the core described in a core structure list previously arranged to identify the structure of each core.

The detailed procedure is as described below.

(i). Acquisition of Information on the Core after the Collision Induced Dissociation In the FT-ICR-mass spectrometry of each fragment ion after the collision induced dissociation, even if a part of the core is the same, each fragment ion having an aliphatic group with about 0 to 4 carbon atoms as the side chain is different in mass according to the type of the side chain, and therefore the fragment ion appears as different peaks. Accordingly, if various mass are preliminarily calculated on the ion having the aliphatic group with about 0 to 4 carbon atoms as the side chain in the core, and the different peaks appeared as described above are compared and matched therewith in various manners, the mass of the core per se can be determined.

In the step 2, on each obtained peak after the collision induced dissociation, such information can be obtained by using this method as: how much mass the core attributed to the peak has, how many hetero atoms such as O, N or S atoms exist, and how many aromatic rings exist from the DBE value.

(ii). Identification of the Structure of the Core after Collision Induced Dissociation Examples of the method for identifying the structure of the core after the collision induced dissociation include a method of preliminarily creating a material in which various cores that can be assumed to form each component molecule of the multicomponent mixture are listed as a model, namely, the "core structure list", and matching information on molecular weight of the core, and the type and the number of hetero atoms stored in the list with information on the core obtained in the above preparation, and selecting the model of the core considered to be most valid from the list to correspond the selected core as the core.

According to this method, the cores are assigned to all the peaks obtained in the FT-ICR-mass spectrometry after the collision induced dissociation, and the structures can be known.

(iii). Core Structure List

The type of the core to be stored in the core structure list described above is not particularly limited, and any type may be stored, in which validity of selection of the core to be stored is directly linked to the validity of identification of the structure of each core.

The "core structure list" is preferably preliminarily created according to a content of the multicomponent mixture per se being a sample. For example, when the multicomponent mixture is the petroleum, a material called the "core structure list for identifying the molecular structure" is preliminarily created on the basis of a lot of findings relating to the petroleum in the past, and the material only needs to be used.

In creating the list, the proper number of cores should be stored in taking into account various conditions such as the number of rings in a basic aromatic ring, a type and the number of naphthene rings directly bonded to the aromatic ring (including a difference of a cata-type or a peri-type), and an aspect of direct bonding (namely, the aspect in which the naphthene ring is bonded to any position of the basic aromatic ring and in any form, and the like).

For example, the list should be created in consideration of convenience of calculation, such as limiting of a size of the aromatic ring to a hexacycle, or limiting of the type of the hetero rings to about 10 by assuming N, O and S as the hetero atom.

(iv). Selection from the Core Structure List

In the core structure list, a plurality of cores which are "same in all of the molecular weight, the DBE value and the type and the number of hetero atoms, but different in the structure formula" exist in several cases. In this case, a rule should be appropriately determined as to which should be selected as first priority of the plurality of cores. Examples of the priority include items 1 to 3 described below.

1. A core consisting of the aromatic ring takes priority.
2. A core having a larger number of unsaturated bonds takes priority.
3. A core having a smaller number of rings takes priority.

(b) Next, the method for identifying the abundance of each core will be described.

As described above, from the height of each obtained peak after the collision induced dissociation in the step 2, m/z thereof, namely, the abundance of the core having the mass can be determined.

The structure of each obtained core after the collision induced dissociation in the step 3 is used later in a step 5, and the abundance of each core after the collision induced dissociation is later used in a step 4.

(4) Step 4 (Estimation of a State of Existence and Abundance of the Core for Each Class) (S4 in FIG. 1)

In the step 4, the molecules attributed to each peak in the step 1 are divided into "classes" on the basis of "the type and the number (including zero) of hetero atoms and the DBE value" to estimate a state of existence and abundance on all the molecules attributed to each relevant "class".

In other words, in the step 4, the molecules attributed to all the peaks in the step 1 are divided into the "classes" on the basis of "the type and the number (including zero) of hetero atoms and the DBE value" in each molecular formula identified in the step 1 to estimate the state of existence and the abundance on all the molecules attributed to each relevant "class".

Hereinafter, the step 4 will be described in detail.

(a) An expression "divided into the "classes" on the basis of "the type and the number of hetero atoms and the DBE value"" means the following. More specifically, in the step 1, the molecular formulas are identified on all the peaks, and therefore the type and the number of hetero atoms in the molecular formula and the DEB value are known. The expression means that each of the molecules attributed to all the peaks is incorporated into each "class" grouped for each of "the type and the number of hetero atoms and the DBE value" on the basis of "the type and the number of hetero atoms and the DBE value".

A term "the type and the number of hetero atoms" means "the number of the hetero atoms for each type of the hetero atoms" in detail. A wording "the type and the number of hetero atoms" herein is used in this meaning. The hetero atom preferably means a nitrogen atom, a sulfur atom and an oxygen atom, and therefore "the type and the number of hetero atoms" can also be preferably referred to as "each number of the nitrogen atoms, the sulfur atoms and the oxygen atoms". Thus, with regard to the hetero atom, "the molecules in which all of the number of the nitrogen atoms, the number of the sulfur atoms and the number of the oxygen atoms are identical" enters the identical "class".

The procedure will be described below in detail.

Originally, in the step 1, the corresponding molecular formula is assigned thereto for each peak of the FT-ICR-mass spectrum. Here, if the molecular formula is known, the type and the number of hetero atoms and the DBE value of the molecule represented by the molecular formula are known. Accordingly, among the molecules attributed to all the peaks, the molecules in which any hetero atom does not exist in the molecular formula are first grouped as a "group of hetero atom zero". Next, on all the molecules existing in the "group of hetero atom zero", the molecules are to be divided for each "DBE value". Thus, all the molecules attributed to original peaks obtained in the FT-ICR-mass spectrum are first divided into the "groups" depending on the type and the number of hetero atoms, and the molecules belonging to the "group" are divided for each "DBE value". The thus newly reorganized unit is taken as the "class".

More specifically, the "group of hetero atom zero" is described in the above description, but in the case of the molecules in which only one nitrogen atom exists as the hetero atom in the molecular formula, the molecules are grouped as an "N1 molecular group", and all the molecules belonging to the "N1 molecular group" only needs to be divided as the "classes" for each "DBE value". In the group, for example, on the "class" in which the molecules having the DBE value=22 are collected, a nomenclature thereof is a "class of DBE value of 22 in the N1 molecular group". In the case of the molecules in which one nitrogen atom and one sulfur atom exist as the hetero atoms in the molecular formula, the molecules are grouped as another group of an "N1S1 molecular group".

The molecules which are the same in "the type and the number of hetero atoms and the DBE value" enter the "identical class", even if the molecular formulas are different because the number of carbons or the number of hydrogens is different.

As described above, the aggregate of the molecules grouped in the unit of the "class" can be expressed as the peak.

(b) Next, an expression "the state of existence is estimated on all the molecules belonging to each relevant "class" means estimation of a matter as to what single core or multicore each molecule belonging to the class is in each class grouped by "the type and the number of hetero atoms and the DBE value" as described above. Moreover, an expression "the abundance is estimated on all the molecules belonging to each relevant "class" means estimation of a matter as to in what proportion each of the single core and the multicore exists.

In performing the estimation described above, the estimation is preferably performed by making several assumptions for convenience of actual calculation.

Here, even the "multicore" may have various combinations depending on what cores are cross-linked and bonded with each other. However, with regard to a sum of the DBE values of the plurality of cores forming the multicore and a sum of the numbers according to the type of hetero atoms, all the molecules belonging to the class have the same values.

(c) "Each molecule belonging to the class consists of what single core or multicore" is preferably estimated as described below.

As described above, on the molecules attributed to each obtained peak in the FT-ICR-mass spectrometry, the molecules are regrouped for each class consisting of the same type and the same number of hetero atoms and the same DBE value, in which the molecules belonging to the class are the single core or the multicore. A method of estimating a matter according to what core the single core or the multicore is formed will be described below.

When the molecule belonging to the class is the single core, the single core having the type and the number of hetero atoms and the DBE value corresponding to the class corresponds thereto. When the molecule belonging to the class is the multicore, such a combination of the cores corresponds thereto, in which a sum of the numbers for each hetero atom of the same type existing in the plurality of cores forming the multicore, and the sum of the DBE values of the plurality of cores coincide with the type and the number of hetero atoms and the DBE value in the class. The sum of the numbers according to the types of hetero atoms of the plurality of cores and the sum of the DBE values only need to correspond to the type and the number of hetero atoms and the DBE value in the class, and therefore the combination of the plurality of cores forming the multicore is not ordinarily limited to one, and a plurality of combinations exist.

The procedure will be described by using an example.

A "group in which the hetero atom does not exist" is taken as an example. In this group, for example, in the case of the molecule in which the DBE value is 22, as the core forming the molecule, first, a single core in which the DBE value is 22 corresponds thereto. Then, if the multicore is first considered by the double core, the double core formed by bonding through cross-linking two cores in which the sum of the DBE values becomes 22 corresponds thereto. Examples of the double core formed by bonding through cross-linking two cores in which the sum of the DBE values is 22 include a double core formed of a core having a DBE value of 12 and a core having a DBE value of 10, a combination of a core having a DBE value of 11 and a core of a DBE value of 11, and a combination of a core having a DBE value of 13 and a core having a DBE value of 9.

Here, all the combinations in which the total becomes 22 should not always be considered. More specifically, the DBE value that can be taken by each core has a certain range. More specifically, in the step 3, the structure of the core existing after the collision induced dissociation is identified, and therefore the DBE value of the core existing after the collision induced dissociation is also known. More specifically, the DBE value that can be taken by each core is within the range of a maximum DBE value and a minimum DBE value of all the cores existing after the collision induced dissociation. In other words, existence of any core having a DBE value out of the range need not be considered. Under this consideration, among the combinations of two cores in which the sum of the DBE value becomes 22, a combination that is unable to exist is known, and therefore such a combination need not be considered.

As the next order, the combination is considered by a triple core, and also in this case, similarly to the case of the double core, the triple core consisting of three cores in which the sum of the DBE value becomes 22 corresponds thereto.

The number of cores forming the "multicore" is not limited, but as the assumption, the multicore formed of three or less cores is preferable. Furthermore, the multicore is further preferably assumed to be formed of two cores. In theory, the multicore in which four or more cores are cross-linked and bonded is considered, but when the number becomes four or more, a possibility of the combinations becomes vast, and in the calculation, the multicore becomes very complicated.

Now, the multicore is described by taking the "group in which the hetero atom does not exist" as the example. In the case of a "group in which the hetero atom exists", in the multicore, the number of types of cores that can be taken becomes vast depending on where the hetero atom exists, more specifically, whether the hetero atom exists in the core, or in the side chain or in the cross-linked part. Accordingly, in the case of the "group in which the hetero atom exists, an assumption "the hetero atom exists only in the core, namely, the hetero atom does not exist in the side chain and the cross-linked part" may be made. Moreover, in the case of a "group in which the plurality of hetero atoms exist", for example, in the case of a "group in which one nitrogen atom and one sulfur atom exist, namely, an N1S1 group", such an assumption as "in the two cores bonded through cross-linking, one nitrogen atom exists in one core, and one sulfur atom exists in the other core" may be appropriately made.

As described above, the state of existence of each molecule belonging to the class, namely, the state in which each molecule consists of what single core or multicore can be estimated.

(d) Next, "in what proportion the single core and the multicore, being each molecule belonging to the class, exist" is preferably estimated by making assumptions as described below.

First, as a first assumption, the abundance of the multicore is assumed to be a product of the abundance of each of the plurality of cores forming the multicore, and the product is taken as an estimated value.

In the above example, among the double cores consisting of a combination of two cores in which the sum of the DBE values becomes 22, for example, the abundance of the double core consisting of the core having the DBE value of 12 and the core having the DBE value of 10 is assumed to be a "product of the abundance of the core having the DBE value of 12 and the abundance of the core having the DBE value of 10 after the CID", and the product is taken as the estimated value.

Here, the abundance of the core having the DBE value of 12 after the CID means a ratio of the height of the peak having the DBE value of 12 after the CID to the total of heights of all the peaks after the CID, and therefore can be calculated if the values already known in the steps 2 and 3 are used.

The abundance of the core having the DBE value of 10 can also be known in a similar manner.

Also on the double core consisting of any other combinations in which the sum of the DBE values becomes 22, for example, the core having the DBE value of 13 and the core having the DBE value of 9, the abundance of the double core can be estimated in a similar manner.

Thus, even on the cores regrouped for each "class" consisting of the molecules which are the same in the type and the number of hetero atoms and the DBE value, the abundance of various multicores belonging to the class can be estimated.

Moreover, as a next assumption, the abundance of the single core in which the DBE value is 22 is assumed to be a value obtained by dividing the abundance of the peak having the DBE value of 22 after the CID by "22" of the DBE value, and the resulting value is preferably taken as the estimated value.

If the value is assumed as described above, the abundance of the single core and various multicores in which the DBE value becomes 22 can be estimated.

(5) Step 5 (Determination of a Core Structure, a Side Chain and a Cross-Link) (S5 in FIG. 1)

In the step 5, the structure of the core forming each molecule is determined on each molecule in which the state of existence is estimated in the step 4, and the side chain and the cross-link are further determined and assigned thereto.

(a) On "each molecule in which the state of existence is estimated in the step 4", an expression "the structure of the core forming each molecule is determined" means that determination is performed by operation (i) to (v) described below.

(i). In the case of the multicore in which the state of existence is estimated in the step 4, the structures are to be viewed by being divided for each core forming the multicore. More specifically, for example, on the multicore in which the DBE value is 22, the multicore is a combination of two cores in such a manner that the sum of the DBE values becomes 22, such as a combination of a core 1 in which the DBE value is 12 and a core 2 in which the DBE value is 10, but the multicore is once canceled. The multicore is canceled on the cores having all the DBE values, and divided into the cores forming the multicore.

(ii). On all the cores in which the state of existence is estimated as the single core in the step 4, and all the cores generated by canceling the multicore as in (i) described above, the cores are regrouped into each "set" for each core which is the same in "the type and the number of hetero atoms and the DBE value".

For example, all the cores are regrouped into a "set" such as a set of "no hetero atom, DBE value=10" and a set of "N=1, DBE value=10", for example. Any core can enter the set of "no hetero atom, DBE value=10", as long as only conditions of "no hetero atom, DBE value=10" are satisfied, and therefore the cores originating from the multicore of the parent from which the core originates, namely, regardless of any multicore before being canceled, or the cores originating from the single core may enter the set.

In addition, the "set" herein is in a concept relating to an original single core and the cores obtained by canceling the multicore, which is different from the "class" relating to the molecule described in the step 4.

(iii). On all the "sets" of "the types and the numbers of hetero atoms and the DBE values" grouped in (ii) described above, specific structures are assigned to all the cores existing in the "sets".

A source of the "structure to be assigned" is the structure of the core identified in the step 3. More specifically, in the step 3, on all the peaks after the CID, the structure, the molecular weight, and the type and the number of hetero atoms and the DBE value of the core attributed thereto are identified, and therefore to a certain "set" of "the type and the number of hetero atoms and the DBE value", the structure of the core attributed to the peak in which "the type and the number of hetero atoms and the DBE value" coincide therewith among all the peaks after the CID is assigned. In this case, only a matter in which "the type and the number of hetero atoms and the DBE value" coincide therewith is the conditions, and therefore if the values coincide therewith, the plurality of relevant peaks exist in several cases. In such a case, a plurality of structures having different molecular weight are assigned to one "set".

(iv). For example, as the structures to be assigned to all the cores belonging to a certain "set" of "the type and the number of hetero atoms and the DBE value", two types of a core X and a core Y (the core Y is assumed to be larger than the core X in mass) are assumed to be assigned thereto according to (iii) described above.

In the cores belonging to the certain "set" of "the type and the number of hetero atoms and the DBE value, the cores each have a "parent serving as an origin", including the cores generated by cutting the cross-link and the side chain in a certain parent molecule by the CID. Then, in the "parent" per se, even if the core is the same, a plurality of cores different in mass exist depending on presence or absence of the side chain and a difference in the number thereof.

Accordingly, first, on the cores belonging to the certain "set" of "the type and the number of hetero atoms and the DBE value", the cores are arranged in order of small mass of the parent to large mass of the parent by using, as the reference, the mass of the parent from which each core originates.

Next, the abundance of the core X and the core Y is already known in the step 3, and therefore in the cores arranged, a line is drawn at the abundance of the core X and the core Y to divide the cores, and the core X is assigned to the cores on a side of small mass, and the core Y is assigned to the cores on a side of large mass.

If three structures of the core X, the core Y and a core Z are identified according to (iii) described above, in a manner similar to the case of the two structures, the cores are divided into three depending on the mass of the parent, the line is drawn at each abundance thereof to divide the cores, and the core X, the core Y and the core Z only need to be assigned thereto sequentially from the side of small mass. A same rule applies also to the case of four or more structures.

According to (i) to (iv) described above, the structure of the core forming each single core or multicore in which the state of existence is estimated in the step 4 is assigned thereto.

(v). After (i) to (iv) described above are performed, the procedure is returned to an original multicore again. If the multicore consists of a combination of the core 1 and the core 2, for example, a certain structure α is identified to the core 1, and a certain structure β is identified to the core 2. As a result, the structure of a part of the core in the multicore is identified.

(b) An expression "the side chain and the cross-link are further determined" means that the procedure is performed by operation of (i) to (iii) described below.

(i). As described above, the structure of the part of the core of the single core or the multicore can be identified, but merely by assuming existence of the part of the core only, the value does not agree with mass represented by m/z of the peak obtained in the FT-ICR-mass spectrometry on a targeted sample. More specifically, even if mass based on carbon, hydrogen and the hetero atom involved in the part of the core is totalized, a difference is produced from the mass represented by m/z of the peak obtained in the FT-ICR-mass spectrometry.

Accordingly, a differential of mass thereof is considered to originate from existence of the side chain bonded to the core and the cross-link bonding the cores with each other, and the number of carbons and the number of hydrogens are calculated so as to eliminate the differential, and the numbers are assigned to the core as the side chain and the cross-link.

For example, to a certain peak of m/z=n, a certain double core formed by cross-linking the core 1 and the core 2 is assumed to be assigned according to the procedure described above. At this time, differential ($d$) of mass thereof=$n$−(mass of the core+ mass of the core 2)

originates from the existence of the side chain and the cross-link.

(ii). According to (i) described above, the number of carbons and the number of hydrogens to be assigned as the side chain and the cross-link can be determined, but what structure of the side chain and the cross-link is unable to be determined yet. Accordingly, in estimating that what structure of the side chain and the cross-link corresponds thereto, in consideration of existence probability of assumed combinations of the side chain and the cross-link, for example, a rule as described below is determined, and the side chain and the cross-link only need to be estimated according to the rule. As the rule, conditions such as an upper limit of the number of carbons forming the side chain or the cross-link, and the number of the side chains only need to be preliminarily determined.

(iii). In (i) described above, when the side chain or the cross-link corresponding to the differential of the mass does not exist, a structure in which the core 1 and the core 2 are simply bonded may be applied thereto.

(c) An expression: the side chain and the cross-link determined as described above are "assigned to the core" does not have a meaning involving determination as to in what position of what core the side chain and the cross-link are bonded.

(d) Thus, according to the step 5, the structure of the core forming each core can be determined on each single core or double core in which the state of existence is estimated in the step 4, and the side chain and the cross-link can be further determined.

(6) Summary of the Step 1 to the Step 5

According to the step 1, the molecular formulas are identified on all the peaks obtained in the mass spectrometry of the multicomponent mixture. According to the step 2 and the step 3, the structure of each core after the CID and the abundance thereof are identified. According to the step 4 and the step 5, the molecules attributed to all the peaks are reorganized as the "class" for each of "the type and the number of hetero atoms and the DBE value" in the molecular formulas identified in the step 1, and the structure of the core forming the molecule and the abundance of the core are determined on all the molecules belonging to each "class". Moreover, according to the step 5, the cross-link and the side chain are also assigned to the core.

Here, in the step 4, if the molecules belonging to the "class" grouped for each of "the type and the number of hetero atoms and the DBE value" are canceled from a group of the "class", each single molecule in which the structure, the abundance, the cross-link and the side chain are already identified is returned to an original peak in the step 1 corresponding to the mass. The molecules having the same molecular formulas return to the same peaks, and therefore a plurality of structures of the molecules may be attributed to one peak.

Thus, the structure of the molecule attributed to the peak and the abundance thereof are identified on each single peak obtained in the mass spectrometry in the step 1.

In summary, according to the step 1 to the step 5, the molecular structure can be identified on each component forming the multicomponent mixture by JACD, and further the abundance can be identified.

In the invention, the multicomponent mixture described above may be one fractionated product obtained by fractionating a certain multicomponent mixture into two or more arbitrary parts. More specifically, when the "multicomponent mixture" in the above description is viewed as one fractionated product I obtained by fractionating a "multicomponent mixture A" in a large group, the "multicomponent mixture A" can be viewed as a mixture of the fractionated products by the number of fractionation, such as a fractionated product I, a fractionated product II and the like. Also on the fractionated product II, the molecular structure of each component forming the fractionated product II can also be identified in the same method as the method performed in the fractionated product I.

In performing the fractionation, a reference to be applied as a boundary of the fractionated product or a method of fractionating the mixture are particularly irrelevant. Specifically, the fractionation is preferably performed by the method as described below.

The method in which separation pretreatment by type with high accuracy is applied to the multicomponent mixture, and the multicomponent mixture is fractionated into a plurality of components is referred to. In particular, in the case of the heavy oil, such fractionation is preferably performed. A method of "separation pretreatment by type" is not particularly limited, and the multicomponent only needs to be separated into several components according to an arbitrary reference. A publicly-known method such as a column chromatographic fractionation method, a Soxhlet extraction method and a high-speed solvent extraction method may be used. In the case of the heavy oil, the column chromatographic fractionation method is preferably used as in the method described in JP-A-2011-133363, for example. A matter as to how many components the multicomponent mixture is fractionated may be appropriately selected according to the purpose.

Specific examples include a method including the following first to third steps.
(First Step)
Heavy oil is separated into a malten fraction soluble in n-paraffin and other insoluble matters.
(Second Step)
The malten fraction separated in (the first step) described above is separated, by using column chromatography, into each fraction of a saturated fraction (Sa), a monocyclic aromatic fraction (1A), a bicyclic aromatic fraction (2A), a tricyclic or more cyclic aromatic fraction (3A+), a polar resin fraction (Po) and a polycyclic aromatic resin fraction (PA).
(Third Step)
The tricyclic or more cyclic aromatic fraction (3A+) obtained in the second step described above may be further preferably separated, by using preparative liquid chromatography, into fractions of a peri-type tetracyclic aromatic fraction and a cata-type tetracyclic aromatic fraction, and a pentacyclic or more cyclic aromatic fraction (5A+) according to circumstances.

Next, the method for determining a composition model of the multicomponent mixture by using a computer will be described.

The method has features of including: a step A of fractionating the multicomponent mixture into two or more arbitrary parts; a step B of identifying the molecular structure of each component forming each fractionated product and the abundance thereof, according to the method described above, on each fractionated product fractionated in the step A; and a step C of integrating the molecular structures of all the components obtained on all the fractionated products and the abundance thereof according to a mixing ratio of each fractionated product fractionated in the step A.

As described above, the "multicomponent mixture A" is viewed as a mixture of the fractionated products by the number of fractions, such as the fractionated product I, the fractionated product II and the like as obtained by fractionating the "multicomponent mixture A", and on each fractionated product, the molecular structure of each component forming the fractionated product and the abundance thereof are identified according to the method described above. Subsequently, if all the components of all the fractionated products are integrated according to the mixing ratio of each of the fractionated product I, the fractionated product II and the like in the "multicomponent mixture A", namely, according to a fraction yield, the mixture being formed of what components and in what proportions can be identified on the composition model as a whole of the "multicomponent mixture A".

Further, the invention relates to a method for estimating values of physical properties of the multicomponent mixture on the basis of the molecular structure of each component forming the multicomponent mixture and the abundance thereof, which are identified according to the method described above.

Specific examples of the "values of physical properties" herein include the following values: such as formation Gibbs free energy, ionization potential, polarizability, permittivity, vapor pressure, liquid density, API degree, gas viscosity, liquid viscosity, surface tension, boiling point, critical temperature, critical pressure, critical volume, heat of formation, heat capacity, dipole moment, enthalpy and entropy.

These values of physical properties are ordinarily calculated by using an atomic group contribution method or a molecular orbital method. The atomic group contribution method means the method in which, in determining the values of physical properties of a certain substance, the chemical structure of the substance is identified, and the values of physical properties of the substance are calculated on the basis of specific parameter values of various atomic groups existing therein, namely, "groups". More specifically, it is assumed that the "groups" of the substance are identified. Moreover, it is assumed that, also in the molecular orbital method, first, the "groups" of the substance are identified, and the structures are identified on the basis thereof.

In the invention, as described above, various atomic groups existing therein are identified on each component forming the multicomponent mixture, and therefore the values of physical properties of the component can be calculated by using publicly-known specific parameter values of various atomic groups. Further, the abundance of each component is also identified, and therefore, if the abundance is taken into consideration, the values of physical properties of the multicomponent mixture as a whole can be appropriately estimated from the values of physical properties of each component.

In operation of refinery equipment of the multicomponent mixture, particularly, the petroleum, optimum conditions are ordinarily set by using the values of physical properties of the petroleum being a raw material as a guideline.

The invention relates to a method of operating equipment relating to the multicomponent mixture, particularly to the petroleum, in which operating conditions are set on the basis of the values of physical properties of the multicomponent mixture estimated as described above. An expression "on the basis of the values of physical properties" also includes such a case where the values of physical properties per se estimated according to the method described above are used alone or in combination of a plurality thereof for setting the operating conditions as a direct factor, or such a case where the values of physical properties estimated according to the method described above are combined with other ordinary values of physical properties to be taken as a factor for determining the operating conditions. Moreover, the expression also widely includes such a case where the values of physical properties estimated according to the method described above do not serve as the direct factor to determine the operating conditions, but are used as data for determining other operation factors.

Next, an embodiment of the invention will be described according to the steps 1 to 5 described above by using a model simulation for convenience in order to facilitate to understand the invention. As the "multicomponent mixture", the polycyclic aromatic resin fraction (PA) is taken as a model.

Hereinafter, the invention is described by schematically simplifying the embodiment using the model simulation, and therefore the invention is not construed in a limiting manner on the basis of the model.

(Points of the Present Method)

The invention relates to a method for identifying the molecular structure of each component forming the multicomponent mixture and the abundance thereof. Specifically, a targeted multicomponent mixture is subjected to the FT-ICR-mass spectrometry to indicate and identify, by JACD, the molecular structure of the molecule (the molecules in several cases) attributed to the peak on each single peak obtained.

Figure 3:
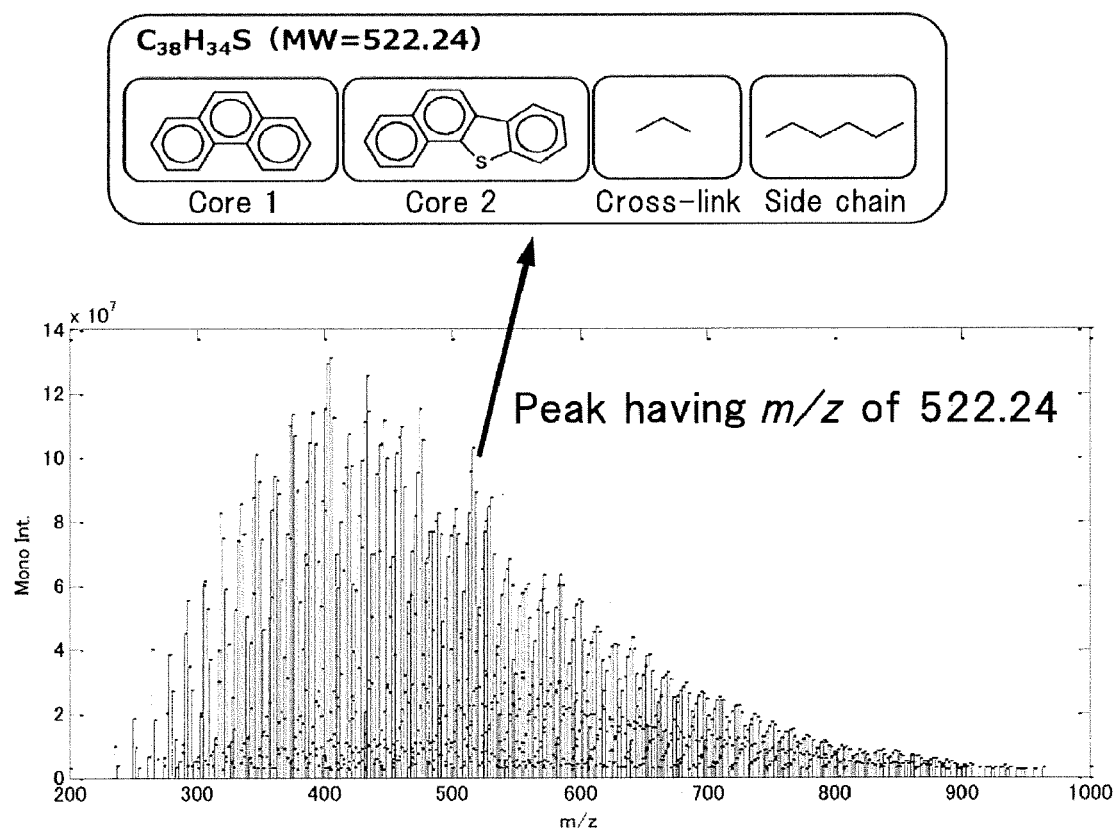
FIG. 3 shows a mass spectrum obtained in FT-ICR-mass spectrometry, and a JACD indication example of molecules attributed to a certain peak.

For example, it is assumed that a certain multicomponent mixture is subjected to the FT-ICR-mass spectrometry, and the mass spectrum is obtained. In this mass spectrum, a great number of peaks are measured. For example, if a peak in which m/z is 522.24 thereamong is taken as an example, the method is applied to identify that "the molecule attributed to this peak has a molecular formula of C38H34S, and JACD indicates that the structure of one molecule corresponding to the molecular formula consists of the core 1, the core 2, the cross-link and the side chain as shown in FIG. 3". Then, when a plurality of molecules corresponding to the molecular formula of C38H34S exist, the method is applied to indicate and identify, by JACD, each structure on all the molecules.

The embodiment will be described by applying each step shown in the flowchart in FIG. 1 to the model simulation.

(1) Step 1 (Mass Spectrometry) (S1 in FIG. 1)

In a step 1, a multicomponent mixture is subjected to mass spectrometry to identify a molecular formula of a molecule attributed to each peak on all the peaks obtained by the spectrometry, and to further identify abundance of the molecule corresponding to the molecular formula, in other words, to identify the molecular formula of each component forming the multicomponent mixture and the abundance of the molecule corresponding to the molecular formula.

In a mass spectrum obtained in the FT-ICR-mass spectrometry, mass can be significantly accurately measured, and therefore the molecular formula of the molecule attributed to each peak can be identified.

Figure 4:
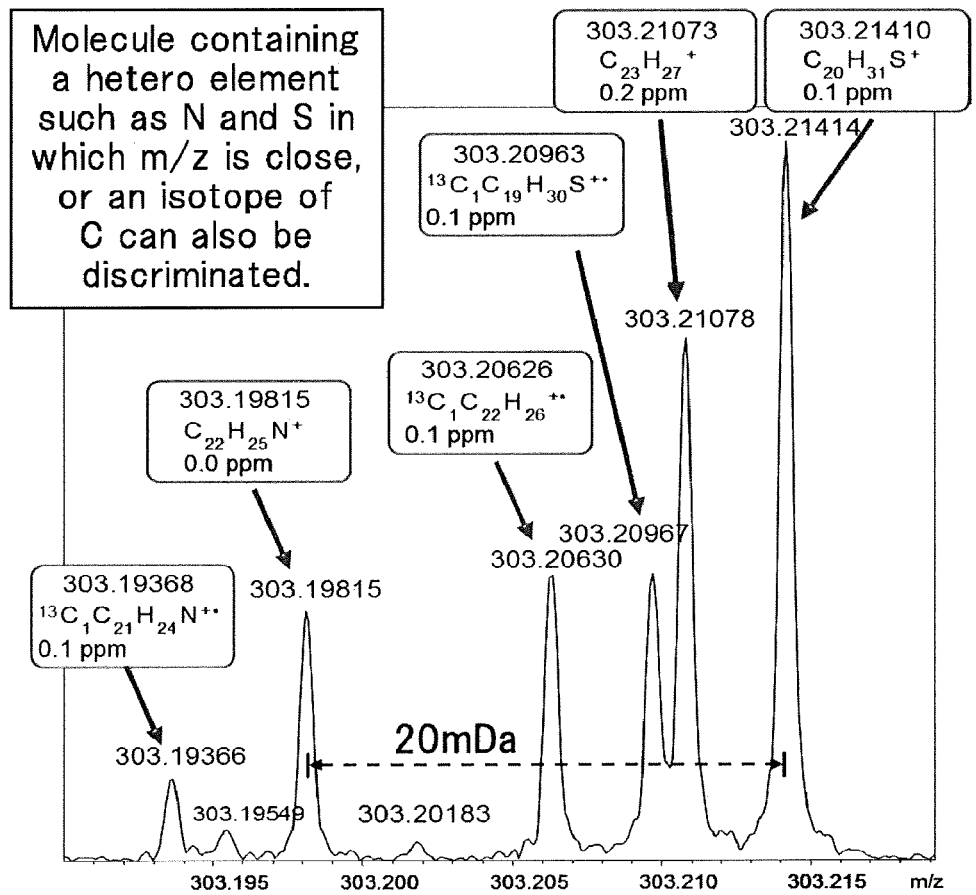
FIG. 4 shows a chart of a mass spectrum obtained in FT-ICR-mass spectrometry.

For example, the chart in FIG. 4 shows that a great number of peaks appear in the vicinity of 303.2 in mass (m/z), but on each peak, the molecular formula of the molecule attributed to the peak can be identified with accuracy.

Moreover, a ratio of the height of a certain peak to a total of heights of all the peaks represents the abundance of the molecule attributed to the peak.

(2) Step 2 (Collision Induced Dissociation (CID)) (S2 in FIG. 1)

In a step 2, the multicomponent mixture is subjected to collision induced dissociation.

Figure 2:
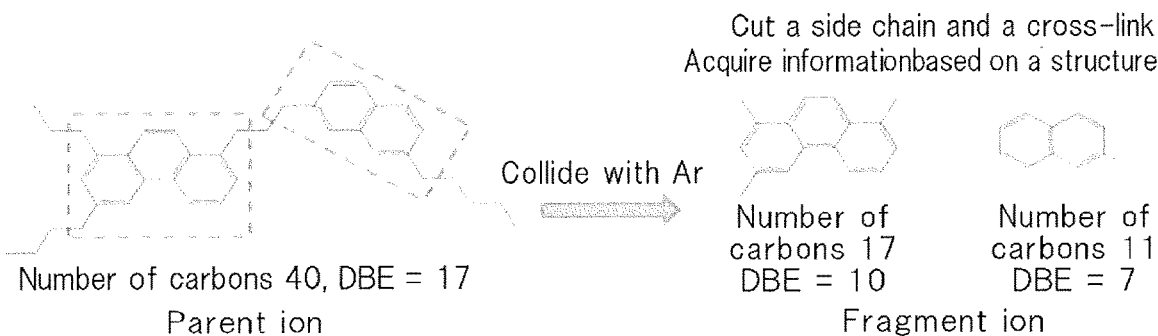
FIG. 2 shows a schematic diagram describing collision induced dissociation.

As shown in FIG. 2, a parent ion having the number of carbons of 40 and DBE=17 is subjected to the collision induced dissociation to cut a side chain and a cross-link to be dissociated into two fragment ions. A DBE value "17" of a molecule (parent ion) before the CID and the sum of the DBE values "10" and "7" of two molecules (fragment ions) after the CID become equal.

As shown in FIG. 2, in most of the molecules having the cross-link, the cross-link and the side chain are cut by the CID, and under suitable conditions, the fragments consist of the core and the side chain having about 4 or less carbon atoms at most.

(3) Step 3 (Identification of a Structure of Each Core and Abundance Thereof) (S3 in FIG. 1)

In a step 3, FT-ICR-mass spectrometry is performed on each fragment ion generated by the CID in the step 2 to identify a structure of a core forming each fragment ion and abundance thereof. More specifically, on peaks obtained by the FT-ICR-mass spectrometry on each fragment ion after the CID, the structure of the core attributed thereto and the abundance thereof are identified.

Figure 5:
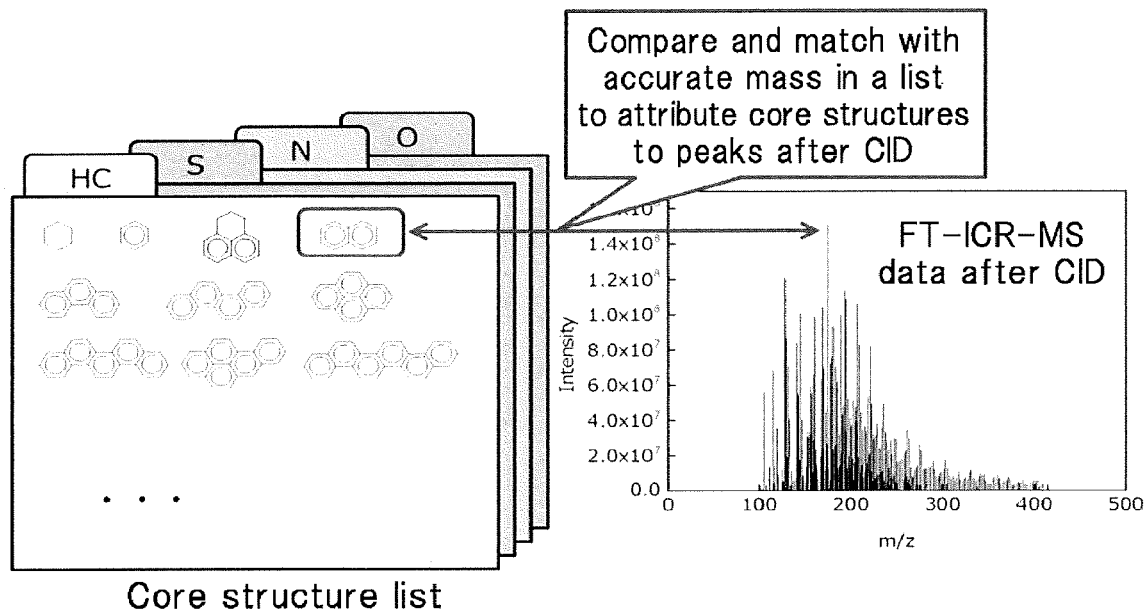
FIG. 5 shows a schematic diagram describing comparison and matching of m/z of a peak obtained in FT-ICR-mass spectrometry after collision induced dissociation with accurate mass in a core structure list.

A method for identifying the structure of each core and the abundance thereof will be described with reference to the schematic diagram in FIG. 5. Here, a value of m/z of the FT-ICR-mass spectrum after the CID and accurate mass of the core stored in the core structure list are compared and matched to attribute the core to each peak. On the above occasion, the core stored in the "core structure list" is matched therewith in such a manner that the molecular weight, the molecular formula and the DBE value obtained from m/z of the peak coincide therewith, and selected and attributed thereto.

Here, on all the peaks of the FT-ICR-mass spectrum after the CID, the structure, the molecular weight, and the type and the number of hetero atoms and the DBE value of the core attributed thereto are identified.

In the core each attributed to the peak, the abundance can also be known from a relative height of the attribution peak.

(4) Step 4 (Estimation of a State of Existence of a Core and Abundance Thereof for Each Class) (S4 in FIG. 1)

In a step 4, the molecules attributed to each peak in the step 1 are divided into "classes" on the basis of "a type and the number (including zero) of hetero atoms and a DBE value" to estimate, on all the molecules belonging to each relevant "class", a state of existence and abundance thereof.

(a) First, as described below, the peaks obtained in the FT-ICR-mass spectrometry of the targeted multicomponent mixture are grouped for each "class" of "the type and the number of hetero atoms and the DBE value" and shown as a peak.

Figure 6:
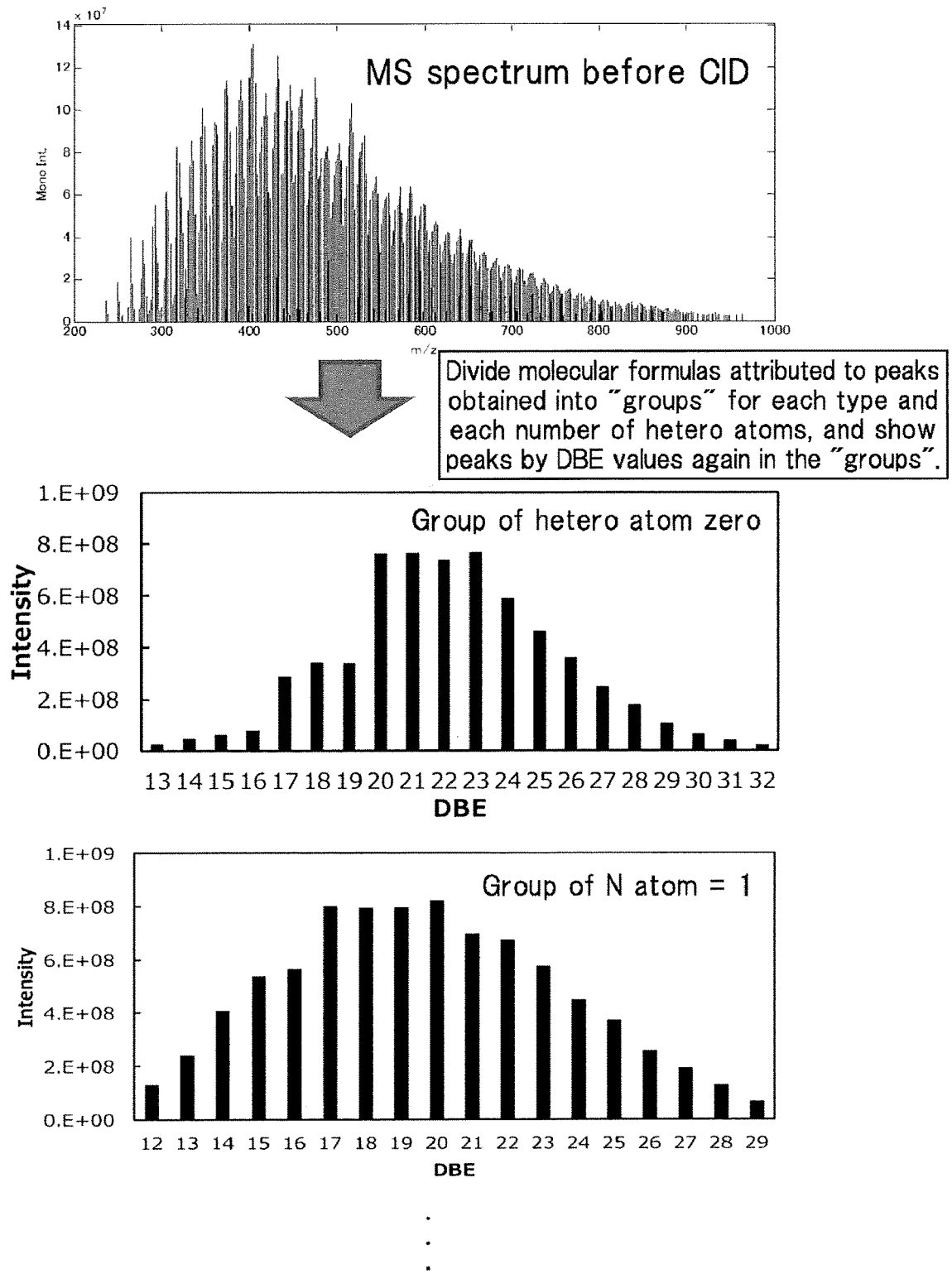
FIG. 6 shows a chart of a mass spectrum obtained in FT-ICR-mass spectrometry on a multicomponent mixture being a sample in a top, and a chart prepared by dividing a molecular formula attributed to a peak obtained into "groups" for each of "a type and the number of hetero atoms, and charts showing peaks by DBE values again in the "groups" in a middle and a bottom.

The procedure will be described with reference to FIG. 6. A top in FIG. 6 shows the "peaks per se obtained by the FT-ICR-mass spectrometry". In the peaks obtained in the FT-ICR-mass spectrometry, the molecular formula of the molecule attributed to the peak, and the type and the number of hetero atoms and the DBE value are known.

Accordingly, first, as shown in a middle in FIG. 6, among all the molecules assigned to all the peaks, the molecules in which the hetero atom does not exist in the molecular formula are first grouped as a "group of hetero atom zero", and then all the molecules existing in the "group of hetero atom zero" are divided for each "DBE value", and shown as the peaks by the DBE values.

Next, as shown in a bottom, the molecules in which one nitrogen atom exists in the molecular formula are grouped as a "group of N atom=1", and then all the molecules existing in the "group of N atom=1" are divided for "each DBE value", and shown as the peaks by the DBE values.

Thus, sequentially, in all of "the groups of the types and the numbers of hetero atoms", the relevant molecules are grouped, all the molecules existing in the group are divided for "each DBE value", and shown as the peaks by the DBE values.

(b) Next, on each of "the DBE values by the peaks" for each group of "the type and the number of hetero atoms", the core forming the peak is estimated.

In this case, for convenience of actual calculation, the estimation is preferably performed by making several assumptions. Here, the procedure will be described by taking "a core having a DBE value=22" as an example.

In the case of the DBE value of 22, examples of cores include a single core in which the DBE value is 22, and a multicore consisting of a plurality of cores in which the sum of the DBE values becomes 22.

Here, an assumption (1) is set as described below.

Assumption (1): "All the multicores are assumed to be formed of two cores, more specifically, only a double core is assumed".

Thus, in the case of DBE=22, the single core consists of one core having DBE=22, and in the double core, the assumed combinations of two cores ("a core A and a core B" herein) are as shown in Table 2 below on the basis of the assumption (1).

Table 2 (The results of the FT-IR-mass spectrometry after the CID show that cores having DBE values of 1 to 5 do not exist, and therefore the cores having DBE values of 1 to 5 need not be considered. Accordingly, examples of combinations of the double core include "16-6, 15-7, 14-8, 13-9, 12-10, and 11-11.")

core A  core B 21  1
20  2
19  3
18  4
17  5
16  6
15  7
14  8
13  9
12  10
11  11

More specifically, the peak of "DBE value=22" is formed of cores as shown in Table 3 below.

TABLE 3

| | | | Abundance | | | | |
|---|---|---|---|---|---|---|---|
| DBE = 22 | DBE = 22 (Single core) | Core A DBE = 12 Core B DBE = 10 | DBE = 11 DBE = 11 | DBE = 14 DBE = 8 | 13 9 | 15 7 | 16 6 |

(c) Next, a matter as to in what proportion each core exists is estimated.

In this estimation, an assumption (2) and an assumption (3) described below are set and determined by dividing cases into a case of (i). double core (multicore) and a case of (ii). single core.

(i). In the case of double core, the assumption (2) is set as described below.

Figure 7:
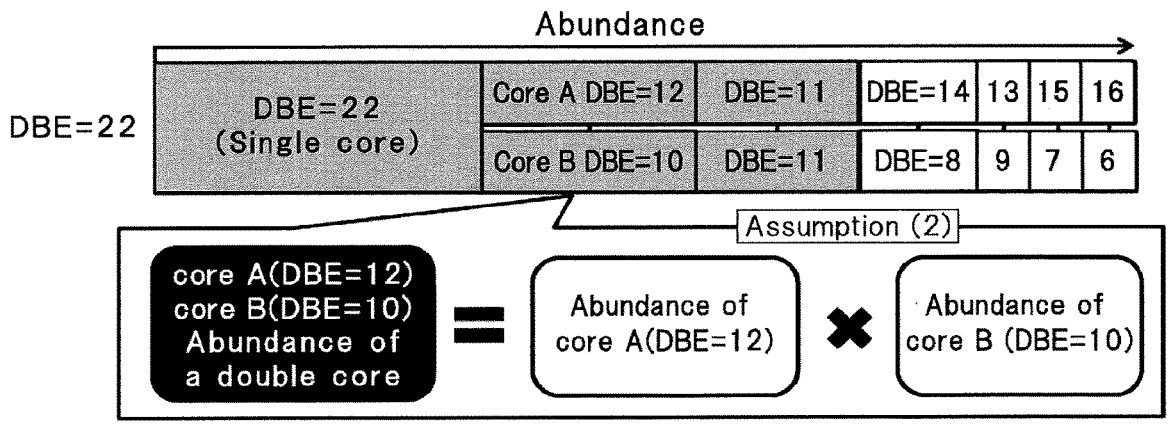
FIG. 7 shows a schematic diagram describing abundance of a multicore.

Assumption (2): In the double core consisting of combinations of two cores in which the sum of the DBE values becomes 22, for example, "abundance of a double core consisting of a core having a DBE value of 12 and a core having a DBE value of 10 is assumed to be the product of the abundance of the core having the DBE value of 12 and the abundance of the core having the DBE value of 10 after the CID", and the value is taken as the estimated value. FIG. 7 schematically shows the abundance of the double core based on the assumption (2).

Here, the abundance of the core having the DBE value of 12 after the CID means a ratio of the height of the peak having the DBE value of 12 to a total of heights of the peaks of all the DBE values.

More specifically, the abundance of the peak having the DBE value of 12 is represented by the ratio: (the total of heights of peaks on the molecule having the DBE value of 12 after the CID)/(the total of heights of all the peaks after the CID).

A same rule applies also to the abundance of the core having the DBE value of 10.

Also on the double core consisting of other combinations of two cores in which the sum of the DBE values becomes 22, for example, a core having a DBE value of 14 and a core having a DBE value of 8, the abundance of the double core can be estimated in a similar manner.

(ii). In the case of single core, the assumption (3) is set as described below.

Figure 8:
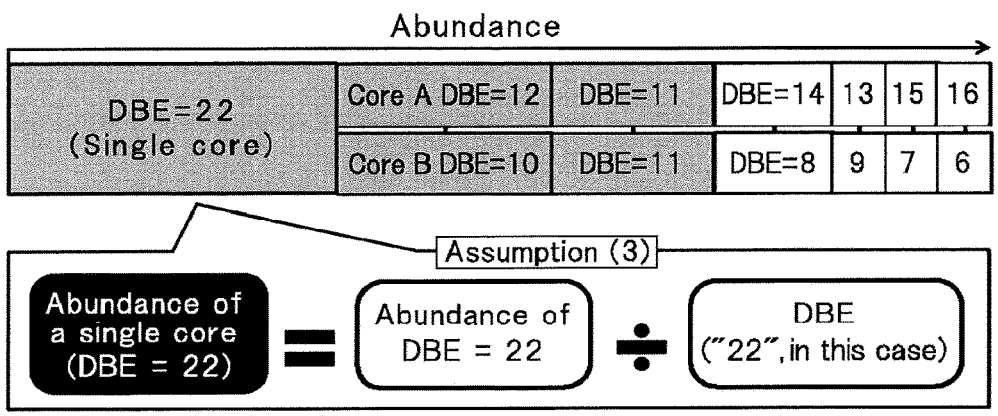
FIG. 8 shows a schematic diagram describing abundance of a single core.

Assumption (3): Abundance of a single core in which a DBE value becomes 22 is assumed to be "a value obtained by dividing abundance of a peak having the DBE value of 22 after the CID by the DBE value of 22". Then, the value obtained by the division is taken as the estimated value. FIG. 8 schematically shows the abundance of the single core based on the assumption (3).

As described above, the abundance of the single core and various double cores in which the DBE value becomes 22 can be estimated.

The case of "DBE value=22 in the group of hetero atom=zero" is described above. In the targeted multicomponent mixture, the cores exist from a DBE value=13 to a DBE value=32 in the case of the hetero atom=zero (middle in FIG. 6), and therefore the state of existence of the core attributed thereto is estimated on each DBE value in a similar manner.

Further, the work described above is performed for each group of all of "the types and the numbers of hetero atoms" existing in a case of N=1, a case of N=2, and the like.

(5) Step 5 (Determination of a Core Structure, a Side Chain and a Cross-Link) (S5 in FIG. 1)

In the step 5, a structure of a core forming each molecule is determined on each molecule in which the state of existence is estimated in the step 4, and a side chain and a cross-link are further determined and assigned thereto.

(a) First, the structure of the core forming each molecule is determined on each molecule in which the state of existence is estimated in the step 4, and assigned thereto. Specifically, the procedure is as described below.

(1) "Preparation"

According to the following procedures (i) to (v), preparatory work of grouping all the cores into each "set" for each of the same cores of "the type and the number of hetero atoms and the DBE value" is performed.

(i). In the case of the double core in which the state of existence is estimated in the step 4, the double core is once canceled and viewed by dividing the double core into each core forming the double core. More specifically, all the cores are viewed as each independent core, obviously including the original single core, and including all the cores generated by canceling the double core.

Figure 9:
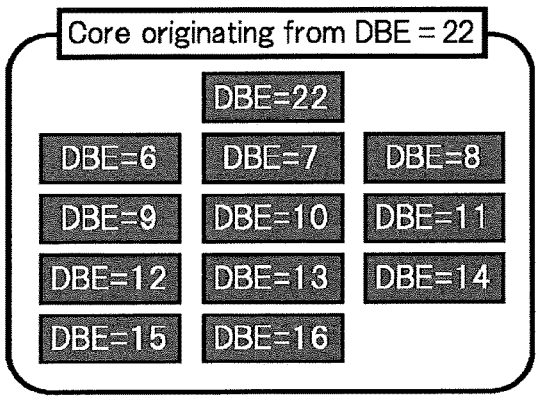
FIG. 9 shows a schematic diagram of cores originating from a DBE value of 22.

For example, in the above example, as shown in FIG. 9, the case of the DBE value=22, the cores are divided into the cores having DBE values of 6, 7, 8, 9, 10, 11, 12, 13, 14, 15, 16 and 22. (In the above example, the results of the FT-ICR-mass spectrometry after the CID show that cores having DBE values=1 to 5 do not exist, and therefore the cores having DBE values=1 to 5 are unnecessary to be considered and can be excluded.)

Also on cores having other DBE values, the double core is canceled and divided into each core forming the double core.

Figure 10:
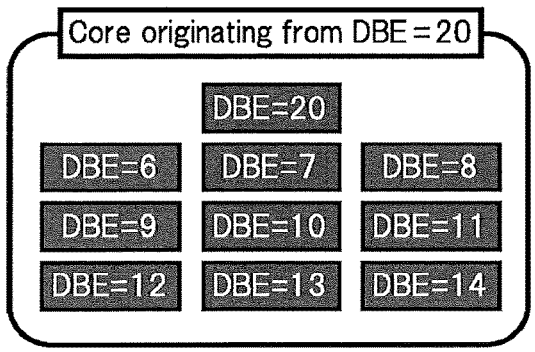
FIG. 10 shows a schematic diagram of cores originating from a DBE value of 20.

As shown in FIG. 10, for example, in the case of a DBE value=20, the cores are divided into cores having DBE values of 6, 7, 8, 9, 10, 11, 12, 13, 14 and 20 in a manner similar to the case of the DBE value of 22.

(ii). Next, the original single core and all the cores generated from the canceled double core are grouped for each DBE value. For example, for a core having the DBE value of 10, all the cores having the DBE value of 10 generated by canceling the double core are collected, regardless of an original double core. All the cores having DBE values of 12 and the like are collected in a similar manner.

Figure 11:
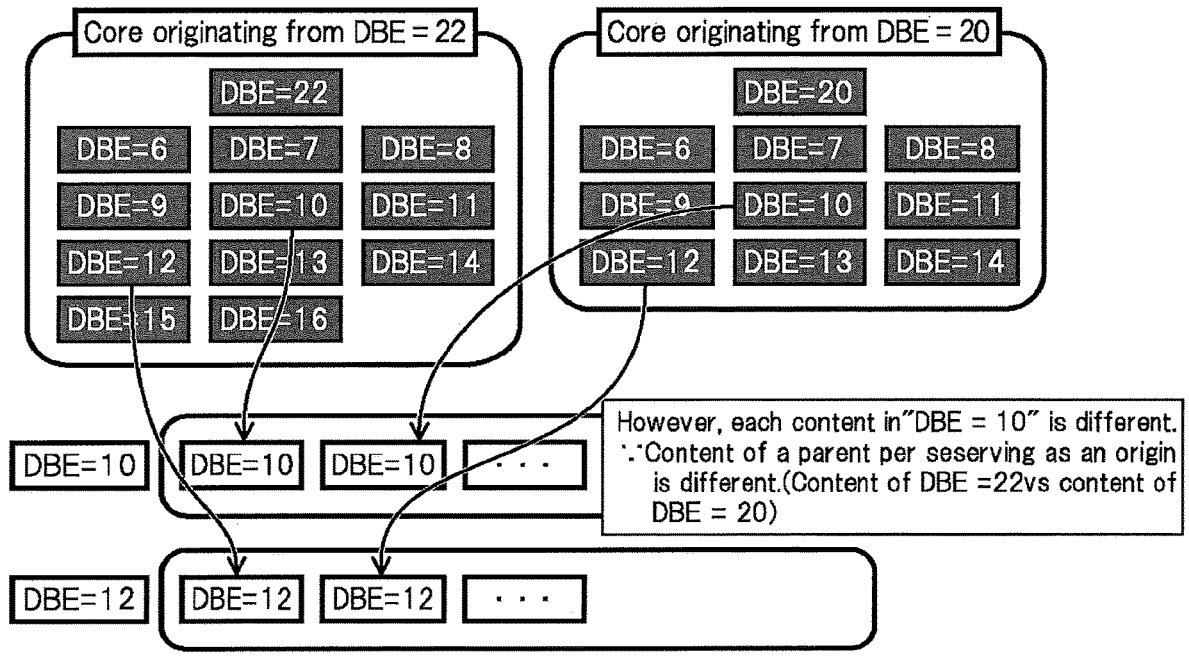
FIG. 11 shows a schematic diagram describing formation of a "set" of cores for each DBE value.

At this time, as shown in FIG. 11, in each of the cores collected as "DBE value=10", each content is different depending on its origin. Each is proportional to the content of the parent serving as the origin (more specifically, the parent is the core having the DBE value=10 originating from the core having the DBE value=22, or the parent is the core having the DBE value=10 originating from the core having the DBE value=20).

(iii). Further, even in the case of "no hetero atom, DBE value=10" and "the DBE value of the parent serving as the origin is also the same 22", when the mass of the peak of the parent is different (more specifically, a plurality of cores which are the same in the core part but different in the mass exist depending on presence or absence of the side chain and a difference in the number thereof), the core becomes another core, and the abundance is also proportional to the abundance in the parent.

(iv). Thus, in the set of "no hetero atom, DBE value=10", a significantly great number of different cores exist depending on what is the parent serving as the origin.

Figure 12:
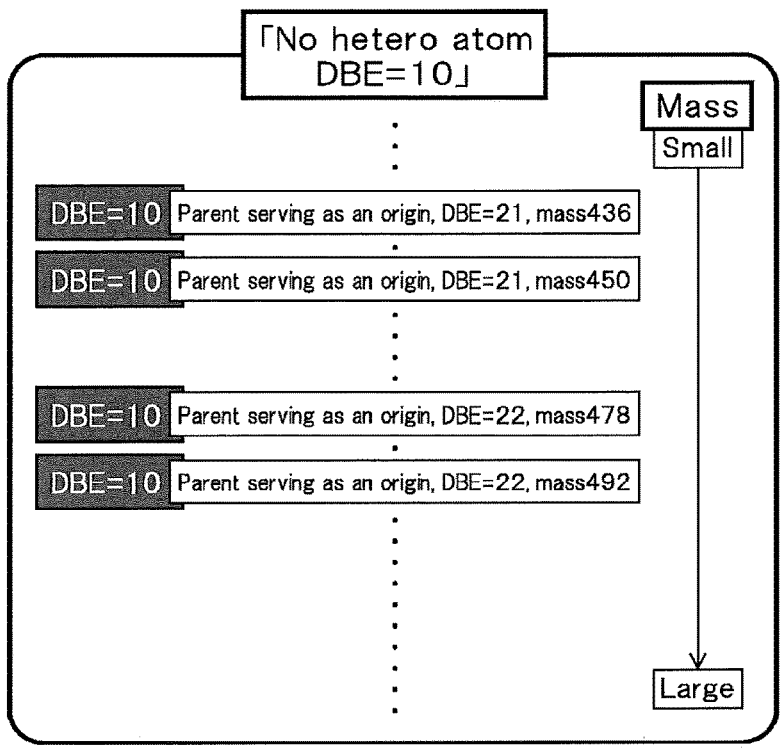
FIG. 12 is a schematic diagram showing arrangement of parents serving as origins in order of mass in a "set" of cores for each DBE value.

Then, as shown in FIG. 12, a great number of these cores are arranged in order of small mass to large mass of the parent on the basis of the mass of the parent serving as the origin.

(v). In the core containing the hetero atom, another "set" is each formed for each of the type and the number of hetero atoms, and the procedure is performed in a manner similar to the above description.

As described above, all the cores are grouped into each "set" for each of the same cores having "the type and the number of hetero atoms and the DBE value", and a diagram in which the cores arranged in order of the mass of the parent from which each core belonging to the set originates has been able to be created.

(2) "Work of Assigning Structures Thereto"

On all the "sets" of "the types and the numbers of hetero atoms and the DBE values" created as described above, structures are assigned to all the cores existing in the sets.

Hereinafter, the procedure will be described by using the set of "no hetero atom, DBE value=10".

(i). The structure is assigned to each of all the cores existing in the "set" of "no hetero atom, DBE value=10". A source of "the structure to be assigned thereto" is the core structure identified in the step 3.

More specifically, in the step 3, on all the peaks after the CID, the structure of the core attributed thereto, the molecular weight, and the type and the number of hetero atoms and the DBE value are identified, and therefore to a certain "set" of "the type and the number of hetero atoms and the DBE value", the core having the peak in which "the type and the number of hetero atoms and the DBE value" coincides therewith among all the peaks after the CID is assigned.

(ii). To all the cores existing in the set of "no hetero atom, DBE value=10", the core having "no hetero atom, DBE value=10" identified in the step 3 is applied.

In the step 3, as the core having "no hetero atom, DBE value=10", only two types of the core X and the core Y having different molecular weight described below are identified from the core structure list, and the abundance is assumed to be 30% in the core X and 70% in the core Y from a ratio of the height of the peak after the CID.

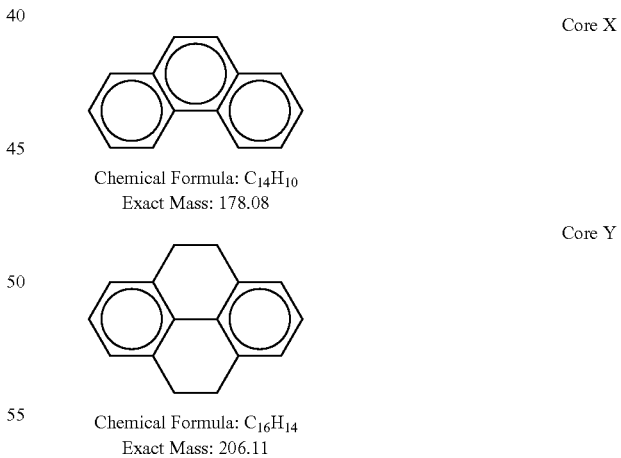

Core X

Chemical Formula: $C_{14}H_{10}$
Exact Mass: 178.08

Core Y

Chemical Formula: $C_{16}H_{14}$
Exact Mass: 206.11

Any of the two types is assigned to the core existing in the set of "no hetero atom, DBE value=10" as the structure.

(iii). How to assign the core X and the core Y to each core existing in the set of "no hetero atom, DBE value=10" is as described below.

Figure 13:
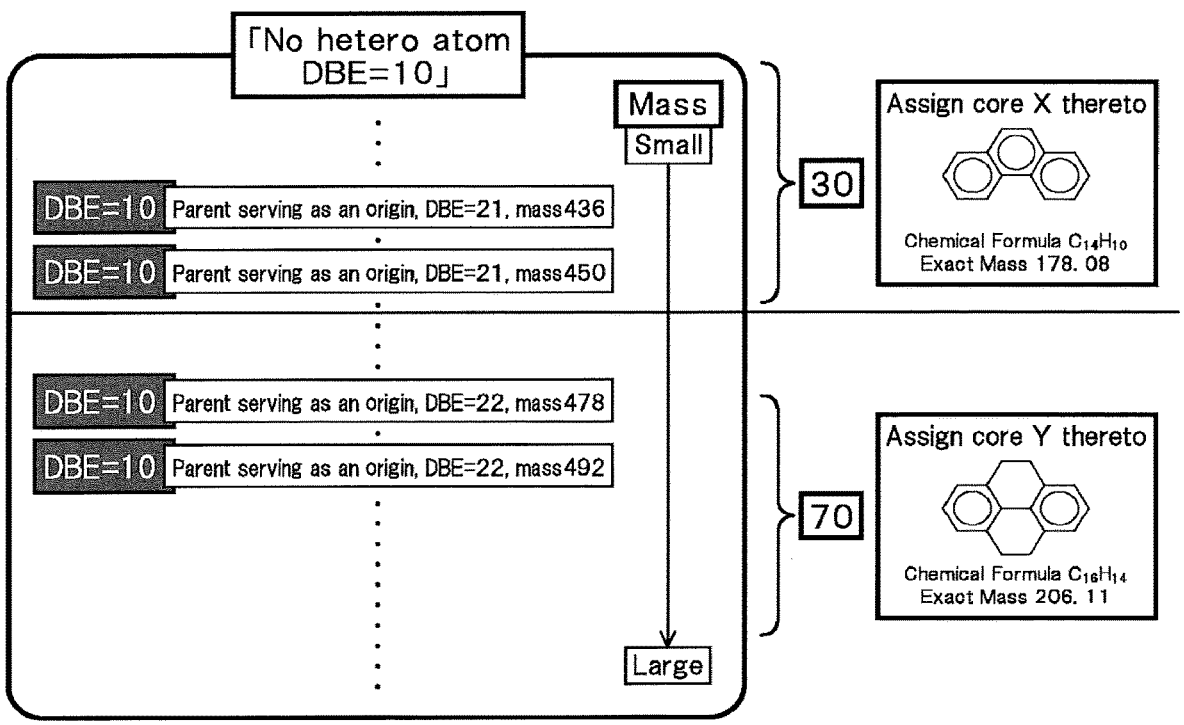
FIG. 13 shows a schematic diagram describing assignment of the cores in FIG. 12.

In "Preparation" described above, the diagram in which the cores are arranged in order from small mass to large mass on the basis of the mass of the parent serving as the origin is arranged. In the diagram in which the cores are arranged, as shown in FIG. 13, a line is drawn at a ratio of the core X to the core Y, namely 30:70 to assign the core X on a side of the small mass, and the core Y on a side of the large mass.

As described above, to all the cores existing in the "set" of "no hetero atom, DBE value=10", the structures are assigned.

(3) "Work of Returning to the Structure of the Multicore"

As described above, all the cores assigned in the structure and the abundance are to be returned to the original double core before the double core is canceled, in which the state of existence is estimated in the step 4.

At this time, for example, in the case of the double core consisting of the core 1 having the DBE value=12 and the core 2 having a DBE value=10, the certain structure a is identified to the core 1 having the DBE value=12 and the certain structure β is identified to the core 2 having the DBE value=10 in (2) described above, and therefore the structure of the core part of this double core is identified. Moreover, the abundance of the core having the structure α and the abundance of the core having the structure β are also identified in the step 3, respectively, and therefore according to the assumption (2) in the step 4 described above, the abundance of the double core having the DBE value=22 is represented and identified by the product of the abundance of the core having the structure a and the abundance of the core having the structure β.

(b) "Work of Determining a Side Chain and a Cross-Link to be Assigned to a Core Type"

Subsequently, according to the following procedures (i) and (ii), the side chain and the cross-link are determined and assigned to the core.

Here, an expression "assigned to the core" does not mean the work involving determining a matter as to in what position of what core the side chain and the cross-link are bonded.

(i). In the above description, the structure of the core part of the single core or the double core and the abundance thereof have been able to be identified, but the side chain bonded to the core or the cross-link bonding the cores with each other is unable to be determined yet.

Incidentally, if only the core part is assumed, the molecular weight does not agree with the value of m/z in the peak obtained in the FT-ICR-mass spectrometry. More specifically, even if the mass based on the carbon, the hydrogen and the hetero atom involving in formation of the core is totalized, a difference is produced from the value of m/z in the peak obtained in the FT-ICR-mass spectrometry.

Accordingly, the differential is considered to originate from existence of the side chain bonded to the core and the cross-link bonding the cores with each other, and the number of carbons and the number of hydrogens are calculated so as to eliminate the differential, and the resulting values are assigned to the core as the side chain and the cross-link.

For example, according to the procedure described above, the structure of the core part consisting of "core 1–core 2" is assumed to be assigned to a certain peak of m/z=n. At this time, differential ($d$) therebetween=$n$−(mass of the core 1+mass of the core 2)

originates from the existence of the side chain and the cross-link.

(ii). In (i) described above, the number of carbons and the number of hydrogens to be assigned as the side chain and the cross-link can be determined, but what structure of the side chain and the cross-link is unable to be determined yet.

Accordingly, in estimating what structure of the side chain and the cross-link corresponds thereto, in consideration of existence probability of the assumed combinations of the side chain and the cross-link, for example, the following rule is determined, and the structure only needs to be estimated according to the rule as described below.

Rule 1: Up to a certain value X in the differential (d) of mass thereof, the structure has no side chain, and originates from only the cross-link.

Rule 2: On a portion more than the certain value X in the differential (d) of mass thereof, the cross-link is assigned thereto according to the rule 1 and then the side chain is assigned thereto. A rule is provided for in the maximum possible number of carbons per one side chain, and the number only needs to be assigned according to the rule.

(c) Thus, on all the core types in which the state of existence is estimated in the step 4, the core structure is determined, and the side chain and the cross-link have been further able to be determined.

In summary, according to the step 1 to the step 5 described above, the molecular structure can be identified, and the abundance thereof can be identified by JACD on each component forming the multicomponent mixture.

Next, Example when separation pretreatment by type was applied to a multicomponent mixture will be described.

(I). Fractionation by Type

As a sample, a vacuum residue (VR) obtained by performing vacuum distillation of an atmospheric residue was used. The vacuum residue (VR) corresponds to heavy oil. Each yield was determine on a saturated fraction (Sa), a monocyclic aromatic fraction (1A), a bicyclic aromatic fraction (2A), a tricyclic or more cyclic aromatic fraction (3A+), each fraction of a polar resin fraction (Po) and a polycyclic aromatic resin fraction (PA), obtained by performing a pretreatment method (first to third steps) to the vacuum residue (VR), and each fraction of an asphaltene fraction (As) separated from a malten fraction in the first step.

In addition, the first to the second steps in the pretreatment method were performed according to the following method.

<First Step: Separation of Malten Fraction>

In a 500 mL-volume Erlenmeyer flask, 7 g of a sample was weighed, 220 mL of n-heptane was added thereto, and the resulting mixture was refluxed and boiled for 1 hour in an n-heptane insoluble matter tester attached with an air cooling tube.

After refluxing and boiling, the resulting mixture was left to stand and cooled, an asphaltene fraction was separated using a filter paper to obtain a fraction containing a malten fraction.

<Second Step: Separation of the Malten Fraction by Column Chromatography>

The malten fraction obtained in the first step was separated by column chromatography under the following conditions.

(1) Column Conditions for Column Chromatography

Column: 15 mm×600 mm (gel packed part, made of glass)

Gel: silica gel: 40 g+alumina gel: 50 g (after activation)

Silica gel: made by Fuji Silysia Chemical Ltd., Chromato Gel Grade 923AR

Alumina gel: made by MP Biomebicals, MP Alumina, Activated, Neutral, Super I

Activation conditions: Silica gel: 250° C.×20 h, alumina gel: 400° C.×20 h, 0.2 kg/cm² ($N_2$ gas) pressurization Sample amount: 1.5 g (malten)

(2) Separation Method

The following solvents were sequentially put in the column to fractionate an eluting solution.

(i) Then, 200 mL of n-heptane was put therein to cut an eluted sample solution up to 250 mL as a saturated fraction (Fr.Sa).
(ii) Then, 250 mL of a mixed solvent of n-heptane 95% and toluene 5% was put therein to cut an eluted sample solution up to 200 mL as a monocyclic aromatic fraction (Fr.1A).
(iii) Then, 250 mL of a mixed solvent of n-heptane 90% and toluene 10% was put therein to cut an eluted sample solution up to 200 mL, and the sample solution was taken as a bicyclic aromatic fraction (Fr.2A).
(iv) Then, 250 mL of toluene was put therein to cut 300 mL of an eluted sample solution, and the sample solution was taken as a tricyclic or more cyclic aromatic fraction (Fr.3A+).
(v) Then, 250 mL of ethanol was put therein to cut 230 mL of an eluted sample solution, and the sample solution was taken as a polar resin fraction (Fr.Po).
(vi) Then, 100 mL of chloroform was put therein, subsequently, (vii) 100 mL of ethanol was put therein, and (vi) and (vii) were repeated again. All portions obtained in (vi) and (vii) were fractionated as one fraction, and the fraction was taken as a polycyclic aromatic resin fraction (Fr.PA).

The results are as described below:

The saturated fraction (Sa): 10%, the monocyclic aromatic fraction (1A): 11%, the bicyclic aromatic fraction (2A): 8%, the tricyclic or more cyclic aromatic fraction (3A+): 35%, the polar resin fraction (Po): 9%, the polycyclic aromatic resin fraction (PA): 16% and the asphaltene fraction (As): 11%.

(II). Identification of Molecular Structure (1) Step 1

A sample was subjected to mass spectrometry by a mass spectrometer according to a Fourier transform ion cyclotron resonance system to identify a molecular formula of a molecule attributed to each peak on all the peaks obtained by the spectrometry, and to further identify abundance of all the molecules corresponding to the peaks.

A detail is as described below.

(a) A SolariX FT-ICR-mass spectrometer having a Fourier transform ion cyclotron resonance system, equipped with a 12 T (tesla) superconducting magnet (made by Bruker Daltonics Inc.) was used.

Measuring conditions are as described below.

Sample used: The polycyclic aromatic resin fraction (PA) obtained by the fractionation by type described above.

Sample preparation method: Tens of milligrams of the sample were dissolved in chloroform, about 1 μL of the resulting mixture was added dropwise to a MALDI (matrix-assisted laser desorption ionization) plate, and after solvent evaporation, the resulting material was taken as a sample for measurement.

Ionization method: Measurement was carried out by using a laser desorption ionization method (LDI method) (shot number: 2000, oscillating frequency: 1000 Hz, power: 23%).

Figure 14:
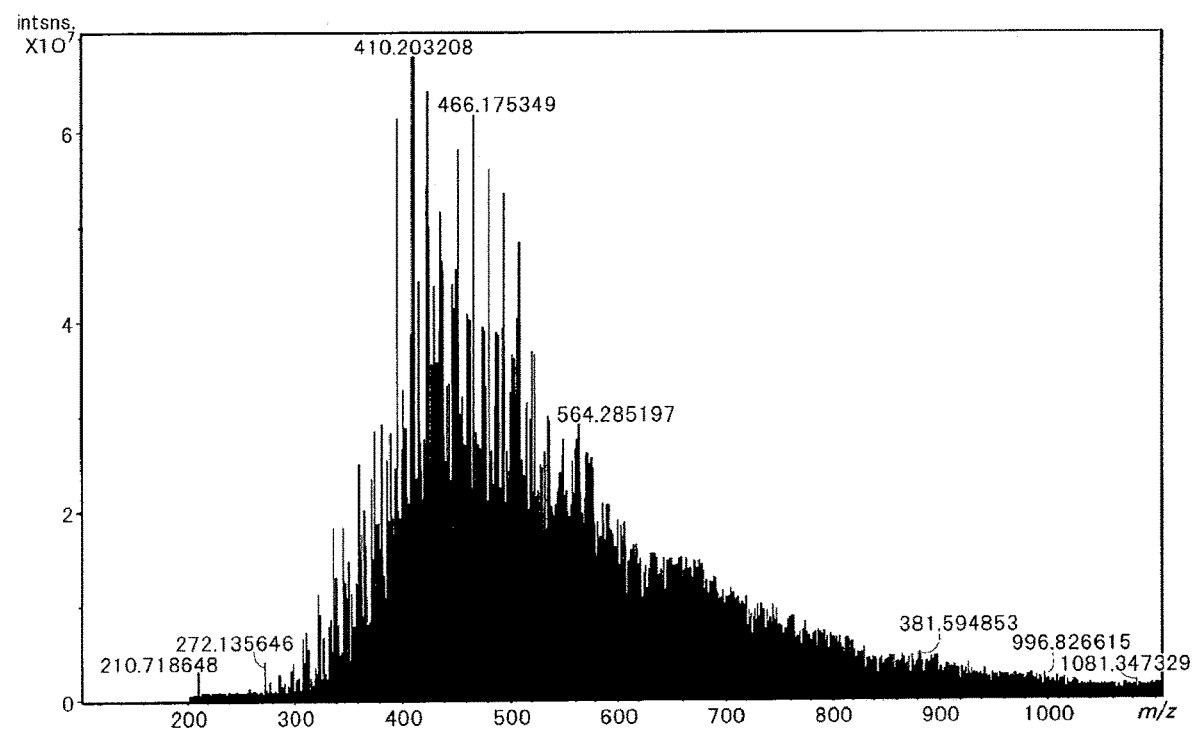
FIG. 14 shows a chart of a mass spectrum obtained by subjecting a polycyclic aromatic resin fraction (PA) to FT-ICR-mass spectrometry.

As a result of the measurement, the mass spectrum shown in FIG. 14 was obtained.

(b) On each peak of the mass spectrum described above, a molecular formula and abundance (expressed in terms of a mole fraction) identified are as shown in Table 4 below.

The number of peaks is 3030. Only a part thereof (peak Nos. 11 to 3022 were omitted) is shown below. In Table 4, the peak Nos. are put in order from a peak having a small m/z value.

TABLE 4

| Peak No. | Number of atoms constituting a molecular formula | | | | | | | Molecular formula | DBE value | Mole fraction |
| | C | H | Hetero atom | | | | | | | |
| | | | N | O | S | V | Ni | | | |
|---|---|---|---|---|---|---|---|---|---|---|
| 1 | 21 | 19 | 1 | 0 | 0 | 0 | 0 | C21H19N | 13 | 0.0000881 |
| 2 | 21 | 21 | 1 | 0 | 0 | 0 | 0 | C21H21N | 12 | 0.0000932 |
| 3 | 22 | 19 | 1 | 0 | 0 | 0 | 0 | C22H19N | 14 | 0.0001107 |
| 4 | 22 | 21 | 1 | 0 | 0 | 0 | 0 | C22H21N | 13 | 0.0001371 |
| 5 | 23 | 19 | 1 | 0 | 0 | 0 | 0 | C23H19N | 15 | 0.0002422 |
| 6 | 23 | 21 | 1 | 0 | 0 | 0 | 0 | C23H21N | 14 | 0.0002583 |
| 7 | 23 | 29 | 1 | 0 | 0 | 0 | 0 | C23H23N | 13 | 0.0001959 |
| 8 | 24 | 19 | 1 | 0 | 0 | 0 | 0 | C24H19N (✗) | 16 | 0.0001215 |
| 9 | 24 | 19 | 1 | 0 | 0 | 0 | 0 | C24H19N (✗) | 16 | 0.0000927 |
| 10 | 24 | 21 | 1 | 0 | 0 | 0 | 0 | C24H21N | 15 | 0.0004335 |
| 11 | 24 | 23 | 1 | 0 | 0 | 0 | 0 | C24H23N | 14 | 0.0003422 |
| 12 | 24 | 25 | 1 | 0 | 0 | 0 | 0 | C24H25N | 13 | 0.0002397 |
| 13 | 22 | 19 | 1 | 0 | 1 | 0 | 0 | C22H19NS | 14 | 0.0000948 |
| 14 | 24 | 27 | 1 | 0 | 0 | 0 | 0 | C24H27N | 12 | 0.0001032 |
| 15 | 26 | 20 | 0 | 0 | 0 | 0 | 0 | C26H2O | 17 | 0.0002390 |
| . | | | | | | | | | | |
| . | | | | | | | | | | |
| . | | | | | | | | | | |
| 3023 | 67 | 91 | 1 | 0 | 1 | 0 | 0 | C67H91NS | 23 | 0.0001157 |
| 3024 | 70 | 93 | 1 | 0 | 0 | 0 | 0 | C70H93N | 25 | 0.0000966 |
| 3025 | 68 | 93 | 1 | 0 | 1 | 0 | 0 | C68H93NS | 23 | 0.0001151 |
| 3026 | 68 | 78 | 0 | 0 | 2 | 0 | 0 | C68H78S2 | 30 | 0.0001061 |
| 3027 | 69 | 87 | 1 | 0 | 1 | 0 | 0 | C69H87NS | 27 | 0.0001097 |
| 3028 | 69 | 95 | 1 | 0 | 1 | 0 | 0 | C69H95NS | 23 | 0.0000974 |
| 3029 | 72 | 105 | 1 | 0 | 0 | 0 | 0 | C72H105N | 21 | 0.0001316 |
| 3030 | 73 | 105 | 1 | 0 | 0 | 0 | 0 | C73H105N | 22 | 0.0000740 |

(✗) Identical as the molecular formula, but in a measurement mechanism of FT-ICR-MS, addition of a hydrogen ion is caused, and the molecular ion appears as another peak. Accordingly, the ion is treated as "a peak having identical m/z."

(2) Step 2

A sample was subjected to collision induced dissociation (CID) to cut a cross-link and a side chain on each component forming the sample.

A detail is as described below.

The sample was prepared and subjected to ionization in the same manner as in the step 1.

As collision induction conditions, collision energy was set to 30 eV.

Figure 15:
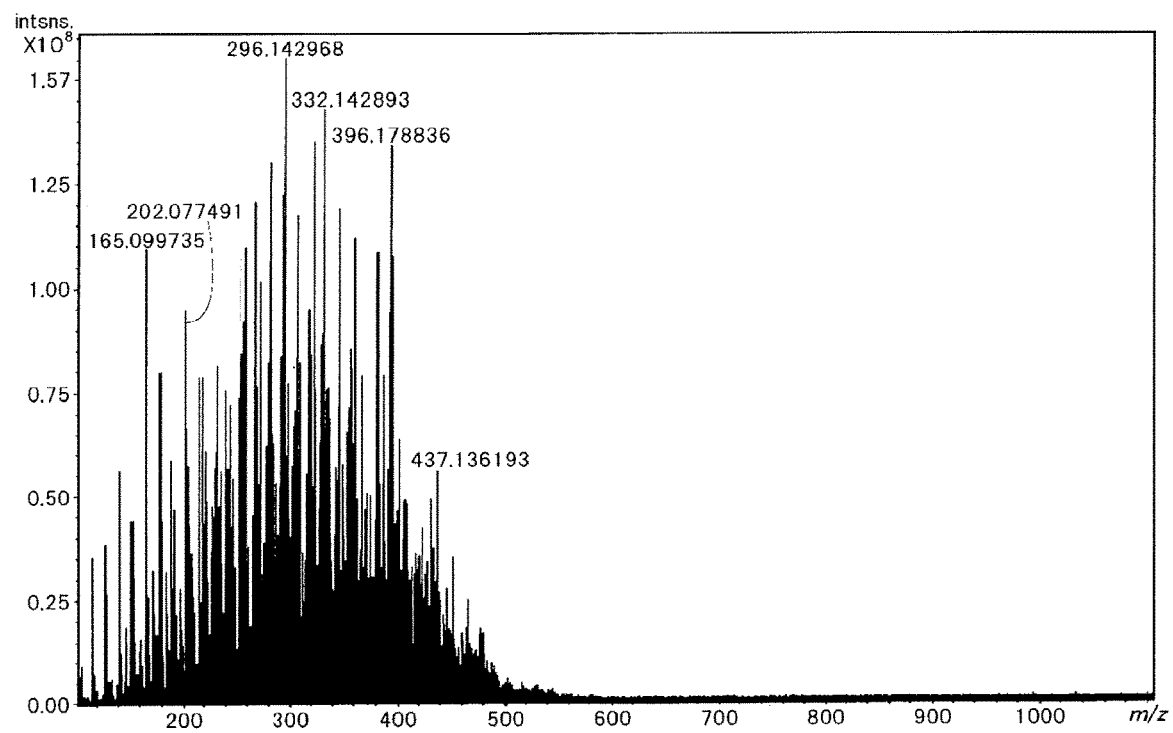
FIG. 15 shows a chart of a mass spectrum obtained by performing FT-ICR-mass spectrometry after a polycyclic aromatic resin fraction (PA) is subjected to collision induced dissociation.

The resulting mass spectrum after the CID is shown in FIG. 15.

(3) Step 3

On each fragment ion generated by the CID in the step 2, FT-ICR-mass spectrometry was performed to identify a structure of a core forming each fragment ion and abundance thereof.

On each peak of the mass spectrum after the CID, molecular weight, a molecular formula and a DBE value of the core stored in a core structure list preliminarily created were matched to identity a structure of each core and abundance thereof.

A part of the core structure list used is shown below.

TABLE 5

Chemical Formula: C$_6$H$_{12}$
Exact Mass: 84.09

1

Chemical Formula: C$_8$H$_6$
Exact Mass: 78.05

2

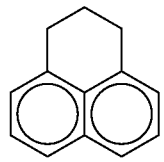

Chemical Formula: C$_{13}$H$_{12}$
Exact Mass: 168.09

3

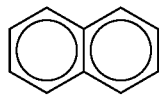

Chemical Formula: C$_{10}$H$_8$
Exact Mass: 128.06

4

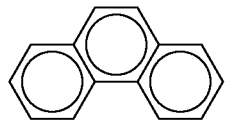

Chemical Formula: C$_{14}$H$_{10}$
Exact Mass: 178.08

5

TABLE 5-continued

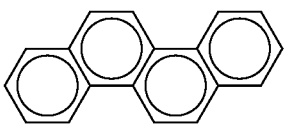

Chemical Formula: C$_{18}$H$_{12}$
Exact Mass: 228.09

6

This step 3 was executed by using a computer by incorporating information on the core structure list into the computer.

(4) Step 4

The molecules attributed to all the peaks each in the step 1 were divided into "classes" on the basis of "a type and the number of hetero atoms and a DBE value" in each molecular formula identified, and on all the molecules belonging to each relevant "class", a state of existence and abundance thereof were estimated.

The step 4 is a process in which data is processed by the computer, and therefore the results are unable to be acquired on the way.

(5) Step 5

A structure of a core forming each molecule was determined on each molecule in which the state of existence was estimated in the step 4, and the side chain and the cross-link were further determined and assigned thereto.

The step 5 is a process in which data is processed by the computer, and therefore the results are unable to be acquired on the way.

(6) Step 6: Identification of a Molecular Structure for a Mass Spectrum of a Sample The number of peaks obtained in the step 1 is 3030, but a plurality of molecules having the same molecular formula are attributed to one peak, namely, the peak representing a certain molecular formula. In the present Example, 38,964 molecules having different structures indicated by JACD were identified for 3030 types of the molecular formulas described above.

Part of the results (peak Nos. 4 to 3028 were omitted) is shown in Table 6 below. How to read the table is as described below.

(a) Peak Nos. are put so as to correspond to peak Nos. in Table 4 shown in the step 1.

Peak No. 1 indicates that the molecule has "C21H19N" as a molecular formula, and that four types of molecules having different structures indicated by JACD are attributed to this molecular formula.

(b) Among the four types of molecules in the molecular formula "C21H19N", for example, if "molecular species No. 1" is described, the structures of the molecules are indicated using alphanumeric characters by JACD.

TABLE 6

| Peak No. | Molecular formula | No. of molecular species identified by JACD | Information relating to a structure (indication using alphanumeric characters by JACD) | | | | | | Mole fraction | Mw |
|---|---|---|---|---|---|---|---|---|---|---|
| | | | Core 1 | Core 2 | Cross-link 1 | Side chain 1 | Side chain 2 | Side chain 3 | | |
| 1 | C21H19N | 1 | 002007 | 004000 | 0BC003 | 000000 | 000000 | 000000 | 0.0000000289 | 285.38131 |
| | | 2 | 004008 | 002001 | 0BC003 | 000000 | 000000 | 000000 | 0.0000000267 | 285.38131 |
| | | 3 | 006008 | 000000 | 000000 | 0SC004 | 000000 | 000000 | 0.0000880393 | 285.38131 |
| | | 4 | 022109 | 000000 | 000000 | 000000 | 000000 | 000000 | 0.0000000104 | 285.38131 |
| 2 | C21H21N | 1 | 002007 | 002001 | 0BC004 | 000000 | 000000 | 000000 | 0.0000000212 | 287.39709 |
| | | 2 | 004008 | 002100 | 0BC002 | 000000 | 000000 | 000000 | 0.0000000054 | 287.39709 |
| | | 3 | 007008 | 000000 | 000000 | 0SC006 | 000000 | 000000 | 0.0000931897 | 287.39709 |
| 3 | C22H19N | 1 | 002007 | 003000 | 0BC002 | 000000 | 000000 | 000000 | 0.0000000267 | 297.39201 |
| | | 2 | 003008 | 002001 | 0BC002 | 000000 | 000000 | 000000 | 0.0000000458 | 297.39201 |
| | | 3 | 004008 | 004000 | 0BC003 | 000000 | 000000 | 000000 | 0.0000000325 | 297.39201 |
| | | 4 | 007007 | 000000 | 000000 | 0SC004 | 000000 | 000000 | 0.0001105349 | 297.39201 |
| | | 5 | 024108 | 000000 | 000000 | 000000 | 000000 | 000000 | 0.0000000507 | 297.39201 |
| . | | | | | | | | | | |
| . | | | | | | | | | | |
| . | | | | | | | | | | |
| 3029 | C72H105N | 1 | 002207 | 070400 | 0BC004 | 0SC010 | 0SC006 | 0SC006 | 0.0000008271 | 984.60555 |
| | | 2 | 002208 | 039301 | 0BC004 | 0SC012 | 0SC006 | 0SC006 | 0.0000004295 | 984.60555 |
| | | 3 | 002407 | 004201 | 0BC004 | 0SC011 | 0SC006 | 0SC006 | 0.0000037081 | 984.60555 |
| | | 4 | 025408 | 000000 | 000000 | 0SC012 | 0SC012 | 0SC008 | 0.0000796676 | 984.60555 |
| | | 5 | 041008 | 005400 | 0BC004 | 0SC011 | 0SC006 | 0SC006 | 0.0000004781 | 984.60555 |
| | | 6 | 041307 | 021100 | 0BC004 | 0SC009 | 0SC006 | 0SC006 | 0.0000115384 | 984.60555 |
| | | 7 | 047307 | 002100 | 0BC004 | 0SC010 | 0SC006 | 0SC006 | 0.0000009256 | 984.60555 |
| | | 8 | 049008 | 004301 | 0BC004 | 0SC010 | 0SC006 | 0SC006 | 0.0000052295 | 984.60555 |
| | | 9 | 049208 | 003200 | 0BC004 | 0SC007 | 0SC006 | 0SC006 | 0.0000099348 | 984.60555 |
| | | 10 | 056308 | 002001 | 0BC004 | 0SC012 | 0SC006 | 0SC006 | 0.0000059571 | 984.60555 |
| | | 11 | 058207 | 002101 | 0BC004 | 0SC009 | 0SC006 | 0SC006 | 0.0000076166 | 984.60555 |
| | | 12 | 070408 | 004100 | 0BC004 | 0SC012 | 0SC007 | 0SC006 | 0.0000053208 | 984.60555 |
| 3030 | C73H105N | 1 | 002207 | 005400 | 0BC004 | 0SC011 | 0SC006 | 0SC006 | 0.0000005168 | 996.61625 |
| | | 2 | 002208 | 024300 | 0BC004 | 0SC012 | 0SC007 | 0SC006 | 0.0000001758 | 996.61625 |
| | | 3 | 002407 | 021201 | 0BC004 | 0SC009 | 0SC006 | 0SC006 | 0.0000050099 | 996.61625 |
| | | 4 | 011408 | 000000 | 0BC004 | 0SC012 | 0SC012 | 0SC010 | 0.0000356564 | 996.61625 |
| | | 5 | 041008 | 039301 | 0BC004 | 0SC011 | 0SC006 | 0SC006 | 0.0000003037 | 996.61625 |
| | | 6 | 041307 | 003200 | 0BC004 | 0SC007 | 0SC006 | 0SC006 | 0.0000076104 | 996.61625 |
| | | 7 | 047307 | 002001 | 0BC004 | 0SC012 | 0SC006 | 0SC006 | 0.0000025774 | 996.61625 |
| | | 8 | 048307 | 002100 | 0BC004 | 0SC011 | 0SC006 | 0SC006 | 0.0000006059 | 996.61625 |
| | | 9 | 049008 | 070400 | 0BC004 | 0SC006 | 0SC006 | 0SC006 | 0.0000025465 | 996.61625 |
| | | 10 | 049208 | 021101 | 0BC004 | 0SC008 | 0SC006 | 0SC006 | 0.0000035328 | 996.61625 |
| | | 11 | 056308 | 002101 | 0BC004 | 0SC009 | 0SC006 | 0SC006 | 0.0000045595 | 996.61625 |
| | | 12 | 058207 | 004100 | 0BC004 | 0SC009 | 0SC006 | 0SC006 | 0.0000044312 | 996.61625 |
| | | 13 | 070408 | 004200 | 0BC004 | 0SC010 | 0SC006 | 0SC006 | 0.0000064572 | 996.61625 |

(c) In the table above, in order to convert indications using the alphanumeric characters by JACD into structures of cores, cross-links and side chains, a code table for rereading alphanumeric character information into structural information only needs to be prepared. Specific examples include the table as described below.

TABLE 7

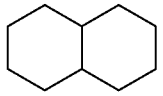 001000

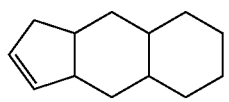 [SMILES: C1=CC2CC3CCCCC3CC2C1] 001001

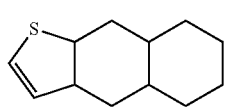 [SMILES: C1=CC2CC3CCCCC3CC2S1] 001002

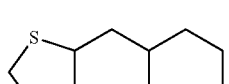 001003

TABLE 7-continued

001100

001101

001102

001103

TABLE 7-continued
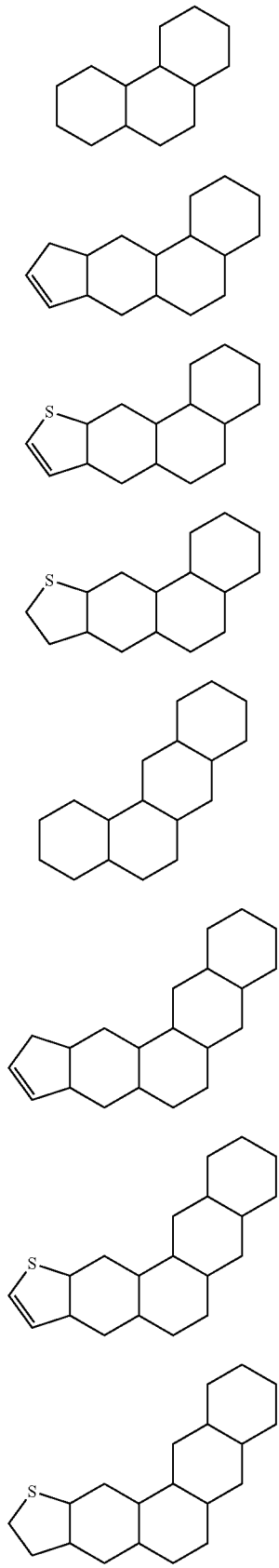
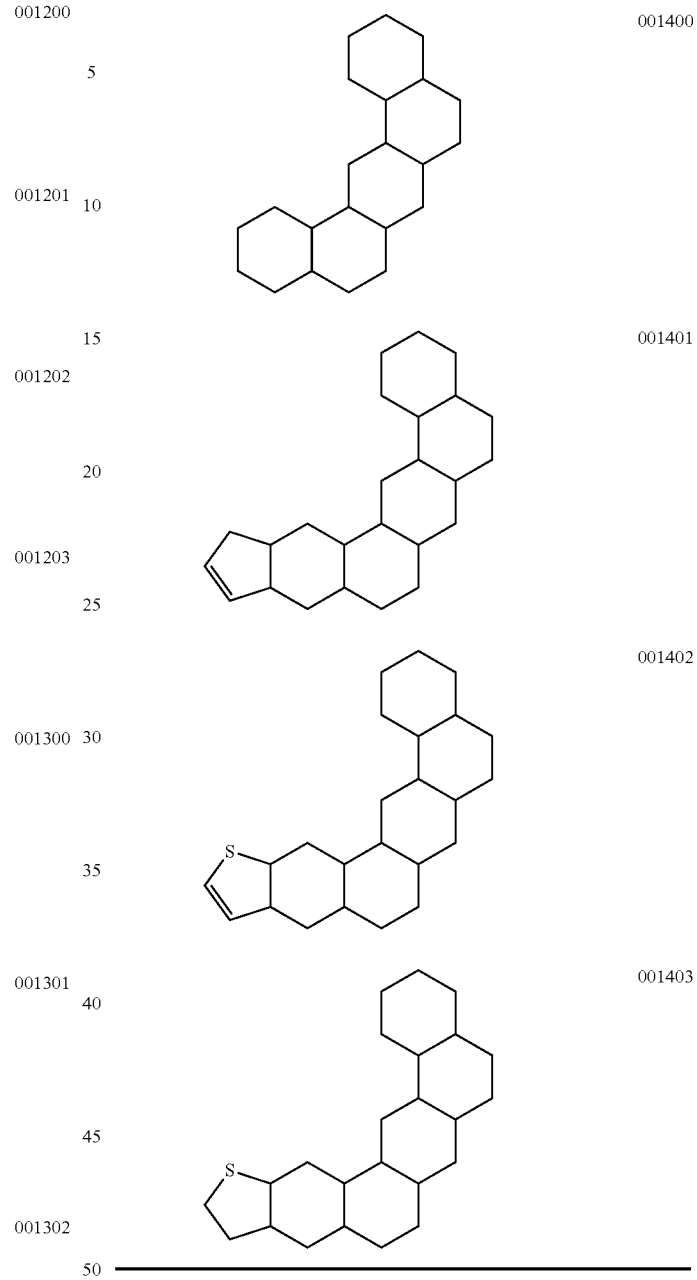
(d) If this table is used, the structure of the molecule in "molecular species No. 1" of the molecular formula "C21H19N" is as described below.
(i). A core 1 is indicated by "002007", and therefore has the following structure.
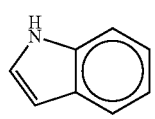
002007
(ii). A core 2 is indicated by "004000", and therefore has the following structure.

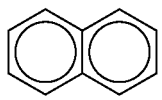

004000

(iii). A cross-link 1 is indicated by "OBC003", and therefore has the following structure.

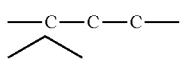

OBC003

(iv). All the side chains are represented by "000000", and therefore the indication means that the side chains do not exist.

(v). Thus, on the molecule in molecular species No. 1" of the molecular formula "C21H19N", the structure was able to be indicated, and identified by JACD.

(e) On all the molecules, the structures were able to be indicated, and identified by JACD in a similar manner.

(III). Integration of Data of Each Fractionated Product (1) Also on the saturated fraction (Sa), the monocyclic aromatic fraction (1A), the bicyclic aromatic fraction (2A), the tricyclic or more cyclic aromatic fraction (3A+), the polar resin fraction (Po) and the asphaltene fraction (As), molecular structures were identified in the same manner as in being performed on the polycyclic aromatic resin fraction except that the following conditions were changed.

(a) On an ionization method for the saturated fraction, the monocyclic aromatic fraction, the bicyclic aromatic fraction, the tricyclic or more cyclic aromatic fraction and the polar resin fraction, measurement was carried out by an atmospheric pressure photoionization method (APPI method) (sample flow rate: 200 μL/h, ion accumulation time: 0.2 sec., number of times of accumulation: 100 times).

(b) On an ionization method for the asphaltene fraction, measurement was carried out by a laser desorption ionization method (LDI method) (shot number: 5000, oscillating frequency: 1000 Hz, power: 17%).

(2) Integration of all the fractionated products: On the saturated fraction (Sa), the monocyclic aromatic fraction (1A), the bicyclic aromatic fraction (2A), the tricyclic or more cyclic aromatic fraction (3A+), the polar resin fraction (Po), the polycyclic aromatic resin fraction (PA) and the asphaltene fraction (As), the molecular structures and the abundance of all the components on all the fractionated products were integrated according to each yield (abundance) obtained as described above.

(3) As described above, on the vacuum residue (VR) being the sample, the molecular structures and the abundance of all the molecules forming the vacuum residue (VR) were able to be identified.

As described above, the embodiments of the invention are described, but the invention is not limited to the embodiments described above, and various changes can be executed in the scope of the invention. In the embodiments described above, the FT-ICR-mass spectrometry has been used as the mass spectrometry, but the embodiments are not limited thereto.

INDUSTRIAL APPLICABILITY

According to the invention, a structure of a molecule forming petroleum can be identified on the petroleum, and therefore the invention can be widely applied in analyzing various reactions of the petroleum at a molecular level, or the like. Furthermore, conducting an analysis at such a molecular level contributes to significantly improved stability of operation of petroleum refinery facilities and operating efficiency.

The entire contents of documents described in the present specification and the description of the Japanese application serving as a basis of claiming the priority concerning the present application to the Paris Convention are incorporated by reference herein.

The invention claimed is:

1. A method for identifying a molecular structure of each component forming a multicomponent mixture and abundance thereof by using a computer, the method comprising:

(i) subjecting the multicomponent mixture to mass spectrometry to identify a molecular formula of a molecule attributed to each obtained peak, and to further identify the abundance of the molecule;

(ii) subjecting the multicomponent mixture to collision induced dissociation;

(iii) performing mass spectrometry on each fragment ion generated via the collision induced dissociation in the subjecting (ii) to identify a structure of a core forming each fragment ion and abundance thereof using the computer by incorporating information on a core structure list into the computer;

(iv) using the computer, dividing the molecules attributed to each peak in the subjecting (i) into classes based on a type and the number, including zero, of hetero atoms and a DBE value, and on all the molecules belonging to each class, estimating a state of existence and the abundance, and (v) determining a structure of a core forming each molecule, on each molecule in which the state of existence is estimated in the dividing (iv), and further determining and assigning a side chain and a cross-link thereto, wherein the method is a deterministic method with predetermined accuracy, wherein, in identifying the structure of each core in the performing (iii), the structure of each core is identified by matching information on an obtained core after the collision induced dissociation in the subjecting (ii) with information on a core described in a core structure list preliminarily prepared, and wherein on each molecule in which a state of existence is estimated in the dividing (iv), determining a structure of a core forming each molecule includes performing (a) to (e):

(a) when a multicore in which the state of existence is estimated, structures are to be viewed by being divided for each core forming the multicore;

(b) on all cores in which the state of existence is estimated as the single core in the dividing (iv), and all the cores generated by cancelling the multicore, the cores are regrouped into each set for each core which is the same in the type and the number of hetero atoms and the DBE value;

(c) on all the sets of the types and the numbers of hetero atoms and the DBE values regrouped, specific structures are assigned to all the cores existing in the sets, a source of the structure to be assigned being the structure of the core identified;

(d) the structures to be assigned to all the cores belonging to a certain set of the type and the number of hetero atoms and the DBE value, two or more types of at least a core X and a core Y, the core Y being assumed to be larger than the core X in mass, are assumed to be assigned thereto, and the cores belonging to the certain set of the type and the number of hetero atoms and the DBE value, the cores each have a parent serving as an origin, including the cores generated by cutting a cross-link and side chain in a certain parent molecule by the CID, then, in parent per se, even if the core is the same, a plurality of cores different in mass exist depending on presence or absence of the side chain and a difference in the number thereof, and, first, on the cores belonging to the certain set of the type and the number of hetero atoms and the DBE value, the cores are arranged in order of small mass of the parent to large mass of the parent by using, as reference, the mass of the parent from which each core originates, then an abundance of the core X and the core Y known from the performing mass spectrometry (iii), and therefore in the cores arranged, a line is drawn at the abundance of the core X and the core Y to divide the cores, and the core X is assigned to the cores on a side of small mass, and the core Y is assigned to the cores on a side of large mass, the structure of the core forming each single core or multicore in which the state of existence is estimated in the dividing (iv) is assigned thereto; and (e) after (a) to (d) are performed, returning to an original multicore again.

2. The method of claim 1, wherein, in the core structure list, each type of cores suitable to form each component forming the multicomponent mixture is listed.

3. The method of claim 1, wherein a molecular structure of each component forming the multicomponent mixture is indicated by an attribute including a core, a side chain, a cross-link, and the number of the attributes.

4. The method of claim 1, wherein the state of existence in the dividing (iv) means that, when a molecule belonging to the class is a multicore, the multicore is formed by combining cores in such a manner that a sum of the number for each heteroatom of the same type existing in a plurality of cores forming the multi core and a sum of DBE values of the plurality of cores coincide with types and the number of heteroatoms and the DBE values in the class.

5. The method of claim 1, wherein the abundance in the dividing (iv) means that, when a molecule belonging to the class is a multicore, a product of each abundance of a plurality of cores forming the multicore is taken as the abundance of the multicore.

6. The method of claim 1, wherein the multicomponent mixture is one fractionated product obtained by fractionating a certain multicomponent mixture into two or more arbitrary parts.

7. A method for determining a composition model of a multicomponent mixture by using a computer, the method comprising:
(A) fractionating the multicomponent mixture into two or more arbitrary parts;
(B) identifying a molecular structure of each component forming each fractionated product and abundance thereof, on each fractionated product fractionated in the fractionating (A), by the method of claim 1; and
(C) integrating molecular structures and abundance of all components obtained on all fractionated products, according to a mixing ratio of each fractionated product fractionated in the fractionating (A).

8. A method for estimating values of physical properties of a multicomponent mixture, the method comprising:
estimating the values based on a molecular structure of each component forming the multicomponent mixture and abundance thereof identified by the method of claim 1.

9. A method of operating equipment relating to a multicomponent mixture, the method comprising:
setting operating conditions based on the values of physical properties of the multicomponent mixture estimated by the method of claim 8.

10. The method of claim 1, wherein the multicomponent mixture is petroleum.

11. A non-transitory computer-readable medium, having computer-executable instructions stored thereon for identifying a molecular structure of each component forming a multicomponent mixture and abundance thereof by using a computer, the computer-executable instructions, when executed by a processor, causing the computer to conduct the method of claim 1.

12. The method of claim 1, comprising indicating the structure of the molecule by attribute and the number of attributes without indicating any information as to in what position the attribute is bonded to other attributes,
wherein the attribute is a part forming the molecule, including a core, a cross-link, and/or a side chain, and
wherein the molecule is identified as including all isomers depending on difference in attribute bonding position.

13. The method of claim 1, which does not include probability theory uncertainty.

14. The method of claim 1, wherein the core structure list comprises prior findings relating to the past samples of similar multicomponent mixtures.

15. A method of fractionating a multicomponent mixture, the method comprising:
conducting the method of claim 1; and
fractionating the multicomponent mixture into fractions comprising a first fraction and a second fraction.

16. A distillation method, comprising:
conducting the method of claim 1; and
distilling the multicomponent mixture, thereby separating the multicomponent mixture into fractions.

17. The method of claim 8, wherein the physical properties comprise Gibbs free energy, ionization potential, polarizability, permittivity, vapor pressure, liquid density, API degree, gas viscosity, liquid viscosity, surface tension, boiling point, critical temperature, critical pressure, critical volume, heat of formation, heat capacity, dipole moment, enthalpy, and/or entropy.

18. The method of claim 9, wherein the equipment comprises extracting equipment, reforming equipment, hydrogenation reaction equipment, and/or desulfurization equipment.

19. The method of claim 1, wherein the collision induced dissociation produces a core comprising a monocyclic aromatic fraction, a bicyclic aromatic fraction, a tricyclic or more cyclic aromatic fraction, a polar resin fraction, and/or a polycyclic aromatic resin fraction.

* * * * *

UNITED STATES PATENT AND TRADEMARK OFFICE
CERTIFICATE OF CORRECTION

PATENT NO. : 11,275,053 B2
APPLICATION NO. : 16/340883
DATED : March 15, 2022
INVENTOR(S) : Teruo Suzuki et al.

It is certified that error appears in the above-identified patent and that said Letters Patent is hereby corrected as shown below:

On the Title Page

Item (71), Line 2-3, "JXTG NIPPON OIL & ENERGY CORPORATION" should read --ENEOS Corporation--.

Signed and Sealed this
Second Day of August, 2022

Katherine Kelly Vidal
*Director of the United States Patent and Trademark Office*